(12) United States Patent
Al-Ali

(10) Patent No.: US 10,646,146 B2
(45) Date of Patent: *May 12, 2020

(54) PHYSIOLOGICAL MONITORING DEVICES, SYSTEMS, AND METHODS

(71) Applicant: MASIMO CORPORATION, Irvine, CA (US)

(72) Inventor: Ammar Al-Ali, San Juan Capistrano, CA (US)

(73) Assignee: Masimo Corporation, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/532,065

(22) Filed: Aug. 5, 2019

(65) Prior Publication Data

US 2019/0350506 A1 Nov. 21, 2019

Related U.S. Application Data

(63) Continuation of application No. 16/226,249, filed on Dec. 19, 2018, now Pat. No. 10,470,695, which is a
(Continued)

(51) Int. Cl.
*A61B 5/1455* (2006.01)
*A61B 5/00* (2006.01)
(Continued)

(52) U.S. Cl.
CPC ........ *A61B 5/14552* (2013.01); *A61B 5/0002* (2013.01); *A61B 5/02416* (2013.01);
(Continued)

(58) Field of Classification Search
None
See application file for complete search history.

(56) References Cited

U.S. PATENT DOCUMENTS

| 4,960,128 A | 10/1990 | Gordon et al. |
| 4,964,408 A | 10/1990 | Hink et al. |
| (Continued) | | |

FOREIGN PATENT DOCUMENTS

| CN | 101484065 B | 7/2009 |
| CN | 101564290 B | 10/2009 |
| (Continued) | | |

OTHER PUBLICATIONS

US 8,845,543 B2, 09/2014, Diab et al. (withdrawn)
(Continued)

*Primary Examiner* — Eric F Winakur
*Assistant Examiner* — Marjan Fardanesh
(74) *Attorney, Agent, or Firm* — Knobbe, Martens, Olson & Bear, LLP

(57) ABSTRACT

A non-invasive, optical-based physiological monitoring system is disclosed. One embodiment includes an emitter configured to emit light. A diffuser is configured to receive and spread the emitted light, and to emit the spread light at a tissue measurement site. The system further includes a concentrator configured to receive the spread light after it has been attenuated by or reflected from the tissue measurement site. The concentrator is also configured to collect and concentrate the received light and to emit the concentrated light to a detector. The detector is configured to detect the concentrated light and to transmit a signal representative of the detected light. A processor is configured to receive the transmitted signal and to determine a physiological parameter, such as, for example, arterial oxygen saturation, in the tissue measurement site.

28 Claims, 7 Drawing Sheets

Related U.S. Application Data continuation of application No. 15/195,199, filed on Jun. 28, 2016, now Pat. No. 10,448,871.

(60) Provisional application No. 62/188,430, filed on Jul. 2, 2015.

(51) Int. Cl.
*A61B 5/024* (2006.01)
*A61B 5/145* (2006.01)

(52) U.S. Cl.
CPC ...... *A61B 5/14532* (2013.01); *A61B 5/14546* (2013.01); *A61B 5/4875* (2013.01); *A61B 5/6826* (2013.01); *A61B 5/7278* (2013.01); *A61B 5/742* (2013.01); *A61B 2562/04* (2013.01)

(56) References Cited

U.S. PATENT DOCUMENTS

| | | |
|---|---|---|
| 5,041,187 A | 8/1991 | Hink et al. |
| 5,069,213 A | 12/1991 | Polczynski |
| 5,099,842 A | 3/1992 | Mannheimer et al. |
| 5,163,438 A | 11/1992 | Gordon et al. |
| 5,203,329 A | 4/1993 | Takatani et al. |
| 5,228,449 A | 7/1993 | Christ et al. |
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,462,051 A | 10/1995 | Oka et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,497,771 A | 3/1996 | Rosenheimer |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,564,429 A | 10/1996 | Bornn et al. |
| 5,584,296 A | 12/1996 | Cui et al. |
| 5,590,649 A | 1/1997 | Caro et al. |
| 5,601,079 A | 2/1997 | Wong et al. |
| 5,602,924 A | 2/1997 | Durand et al. |
| 5,623,925 A | 4/1997 | Swenson et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| 5,699,808 A | 12/1997 | John |
| 5,729,203 A | 3/1998 | Oka et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,792,052 A | 8/1998 | Isaacson et al. |
| 5,800,349 A | 9/1998 | Isaacson et al. |
| 5,810,734 A | 9/1998 | Caro et al. |
| 5,823,950 A | 10/1998 | Diab et al. |
| 5,830,131 A | 11/1998 | Caro et al. |
| 5,830,137 A | 11/1998 | Scharf |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,987,343 A | 11/1999 | Kinast |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,102,856 A | 8/2000 | Groff et al. |
| 6,110,522 A | 8/2000 | Lepper, Jr. et al. |
| 6,124,597 A | 9/2000 | Shehada |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,223,063 B1 | 4/2001 | Chaiken et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,680 B1 | 6/2001 | Miwa |
| 6,241,683 B1 | 6/2001 | Macklem et al. |
| 6,253,097 B1 | 6/2001 | Aronow et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,301,493 B1 | 10/2001 | Marro et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,223 B1 | 1/2002 | Chin et al. |
| 6,343,224 B1 | 1/2002 | Parker |
| 6,349,228 B1 | 2/2002 | Kiani et al. |
| 6,356,203 B1 | 3/2002 | Halleck et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |

(56) References Cited

U.S. PATENT DOCUMENTS

| | | |
|---|---|---|
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,526 B1 | 12/2003 | Aoyagi et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,785,568 B2 | 8/2004 | Chance |
| 6,792,300 B1 | 9/2004 | Diab et al. |
| 6,801,799 B2 | 10/2004 | Mendelson |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,831,266 B2 | 12/2004 | Paritsky et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,048,687 B1 | 5/2006 | Reuss et al. |
| 7,060,963 B2 | 6/2006 | Maegawa et al. |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,227,156 B2 | 6/2007 | Colvin, Jr. et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,519,327 B2 | 4/2009 | White |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,601,123 B2 | 10/2009 | Tweed et al. |
| 7,613,490 B2 | 11/2009 | Sarussi et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,726,209 B2 | 6/2010 | Ruotoistenmäki |
| 7,729,733 B2 | 6/2010 | Al-Ali et al. |
| 7,734,320 B2 | 6/2010 | Al-Ali |
| 7,740,588 B1 | 6/2010 | Sciarra |
| 7,740,589 B2 | 6/2010 | Maschke et al. |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |

(56) References Cited

U.S. PATENT DOCUMENTS

| | | |
|---|---|---|
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,862,523 B2 | 1/2011 | Ruotoistenmaki |
| 7,865,222 B2 | 1/2011 | Weber et al. |
| 7,869,849 B2 | 1/2011 | Ollerdessen et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,510 B2 | 3/2011 | Hoarau |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| 8,071,935 B2 | 12/2011 | Besko et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,280,469 B2 | 10/2012 | Baker, Jr. et al. |
| 8,280,473 B2 | 10/2012 | Al-Ali |
| 8,289,130 B2 | 10/2012 | Nakajima et al. |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,364,389 B2 | 1/2013 | Dorogusker et al. |
| 8,374,665 B2 | 2/2013 | Lamego |
| 8,385,995 B2 | 2/2013 | Al-ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,452,364 B2 | 5/2013 | Hannula et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellot et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,496,595 B2 | 7/2013 | Jornod |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,515,515 B2 | 8/2013 | McKenna et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,591,426 B2 | 11/2013 | Onoe et al. |
| 8,600,467 B2 | 12/2013 | Al-Ali et al. |
| 8,606,342 B2 | 12/2013 | Diab |
| 8,615,290 B2 | 12/2013 | Lin et al. |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,655,004 B2 | 2/2014 | Prest et al. |
| 8,663,107 B2 | 3/2014 | Kiani |
| 8,666,468 B1 | 3/2014 | Al-Ali |
| 8,667,967 B2 | 3/2014 | Al-Ali et al. |

(56) References Cited

U.S. PATENT DOCUMENTS

| | | |
|---|---|---|
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,690,799 B2 | 4/2014 | Telfort et al. |
| 8,700,111 B2 | 4/2014 | LeBoeuf et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,760,517 B2 | 6/2014 | Sarwar et al. |
| 8,761,850 B2 | 6/2014 | Lamego |
| 8,764,671 B2 | 7/2014 | Kiani |
| 8,768,423 B2 | 7/2014 | Shakespeare et al. |
| 8,768,426 B2 | 7/2014 | Haisley et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,838,210 B2 | 9/2014 | Wood et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,920,332 B2 | 12/2014 | Hong et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,437 B2 | 7/2015 | Paalasmaa |
| 9,072,474 B2 | 7/2015 | Al-Ali et al. |
| 9,078,560 B2 | 7/2015 | Schurman et al. |
| 9,081,889 B2 | 7/2015 | Ingrassia, Jr. et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,210,566 B2 | 12/2015 | Ziemianska et al. |
| 9,211,072 B2 | 12/2015 | Kiani |
| 9,211,095 B1 | 12/2015 | Al-Ali |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,311,382 B2 | 4/2016 | Varoglu et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,339,236 B2 | 5/2016 | Frix et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,357,665 B2 | 5/2016 | Myers et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-ali et al. |
| 9,375,185 B2 | 6/2016 | Ali et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,466,919 B2 | 10/2016 | Kiani et al. |
| 9,474,474 B2 | 10/2016 | Lamego et al. |
| 9,480,422 B2 | 11/2016 | Al-Ali |
| 9,480,435 B2 | 11/2016 | Olsen |
| 9,489,081 B2 | 11/2016 | Anzures et al. |
| 9,492,110 B2 | 11/2016 | Al-Ali et al. |
| 9,497,534 B2 | 11/2016 | Prest et al. |
| 9,510,779 B2 | 12/2016 | Poeze et al. |
| 9,517,024 B2 | 12/2016 | Kiani et al. |

(56) References Cited

U.S. PATENT DOCUMENTS

| | | |
|---|---|---|
| 9,526,430 B2 | 12/2016 | Srinivas et al. |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,553,625 B2 | 1/2017 | Hatanaka et al. |
| 9,554,737 B2 | 1/2017 | Schurman et al. |
| 9,560,996 B2 | 2/2017 | Kiani |
| 9,560,998 B2 | 2/2017 | Al-Ali et al. |
| 9,566,019 B2 | 2/2017 | Al-Ali et al. |
| 9,579,039 B2 | 2/2017 | Jansen et al. |
| 9,591,975 B2 | 3/2017 | Dalvi et al. |
| 9,593,969 B2 | 3/2017 | King |
| 9,622,692 B2 | 4/2017 | Lamego et al. |
| 9,622,693 B2 | 4/2017 | Diab |
| D788,312 S | 5/2017 | Al-Ali et al. |
| 9,636,055 B2 | 5/2017 | Al-Ali et al. |
| 9,636,056 B2 | 5/2017 | Al-Ali |
| 9,649,054 B2 | 5/2017 | Lamego et al. |
| 9,651,405 B1 | 5/2017 | Gowreesunker et al. |
| 9,662,052 B2 | 5/2017 | Al-Ali et al. |
| 9,668,676 B2 | 6/2017 | Culbert |
| 9,668,679 B2 | 6/2017 | Schurman et al. |
| 9,668,680 B2 | 6/2017 | Bruinsma et al. |
| 9,668,703 B2 | 6/2017 | Al-Ali |
| 9,675,286 B2 | 6/2017 | Diab |
| 9,681,812 B2 | 6/2017 | Presura |
| 9,684,900 B2 | 6/2017 | Motoki et al. |
| 9,687,160 B2 | 6/2017 | Kiani |
| 9,693,719 B2 | 7/2017 | Al-Ali et al. |
| 9,693,737 B2 | 7/2017 | Al-Ali |
| 9,697,928 B2 | 7/2017 | Al-Ali et al. |
| 9,699,546 B2 | 7/2017 | Qian et al. |
| 9,716,937 B2 | 7/2017 | Qian et al. |
| 9,717,425 B2 | 8/2017 | Kiani et al. |
| 9,717,448 B2 | 8/2017 | Frix et al. |
| 9,717,458 B2 | 8/2017 | Lamego et al. |
| 9,723,997 B1 | 8/2017 | Lamego |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,730,640 B2 | 8/2017 | Diab et al. |
| 9,743,887 B2 | 8/2017 | Al-Ali et al. |
| 9,749,232 B2 | 8/2017 | Sampath et al. |
| 9,750,442 B2 | 9/2017 | Olsen |
| 9,750,443 B2 | 9/2017 | Smith et al. |
| 9,750,461 B1 | 9/2017 | Telfort |
| 9,752,925 B2 | 9/2017 | Chu et al. |
| 9,775,545 B2 | 10/2017 | Al-Ali et al. |
| 9,775,546 B2 | 10/2017 | Diab et al. |
| 9,775,570 B2 | 10/2017 | Al-Ali |
| 9,778,079 B1 | 10/2017 | Al-Ali et al. |
| 9,781,984 B2 | 10/2017 | Baranski et al. |
| 9,782,077 B2 | 10/2017 | Lamego et al. |
| 9,782,110 B2 | 10/2017 | Kiani |
| 9,787,568 B2 | 10/2017 | Lamego et al. |
| 9,788,735 B2 | 10/2017 | Al-Ali |
| 9,788,768 B2 | 10/2017 | Al-Ali et al. |
| 9,795,300 B2 | 10/2017 | Al-Ali |
| 9,795,310 B2 | 10/2017 | Al-Ali |
| 9,795,358 B2 | 10/2017 | Telfort et al. |
| 9,795,739 B2 | 10/2017 | Al-Ali et al. |
| 9,801,556 B2 | 10/2017 | Kiani |
| 9,801,588 B2 | 10/2017 | Weber et al. |
| 9,808,188 B1 | 11/2017 | Perea et al. |
| 9,814,418 B2 | 11/2017 | Weber et al. |
| 9,820,691 B2 | 11/2017 | Kiani |
| 9,833,152 B2 | 12/2017 | Kiani et al. |
| 9,833,180 B2 | 12/2017 | Shakespeare et al. |
| 9,838,775 B2 | 12/2017 | Qian et al. |
| 9,839,379 B2 | 12/2017 | Al-Ali et al. |
| 9,839,381 B1 | 12/2017 | Weber et al. |
| 9,847,002 B2 | 12/2017 | Kiani et al. |
| 9,847,749 B2 | 12/2017 | Kiani et al. |
| 9,848,800 B1 | 12/2017 | Lee et al. |
| 9,848,806 B2 | 12/2017 | Al-Ali et al. |
| 9,848,807 B2 | 12/2017 | Lamego |
| 9,848,823 B2 | 12/2017 | Raghuram et al. |
| 9,861,298 B2 | 1/2018 | Eckerbom et al. |
| 9,861,304 B2 | 1/2018 | Al-Ali et al. |
| 9,861,305 B1 | 1/2018 | Weber et al. |
| 9,866,671 B1 | 1/2018 | Thompson et al. |
| 9,867,575 B2 | 1/2018 | Maani et al. |
| 9,867,578 B2 | 1/2018 | Al-Ali et al. |
| 9,872,623 B2 | 1/2018 | Al-Ali |
| 9,876,320 B2 | 1/2018 | Coverston et al. |
| 9,877,650 B2 | 1/2018 | Muhsin et al. |
| 9,877,686 B2 | 1/2018 | Al-Ali et al. |
| 9,891,079 B2 | 2/2018 | Dalvi |
| 9,891,590 B2 | 2/2018 | Shim et al. |
| 9,895,107 B2 | 2/2018 | Al-Ali et al. |
| 9,898,049 B2 | 2/2018 | Myers et al. |
| 9,913,617 B2 | 3/2018 | Al-Ali et al. |
| 9,918,646 B2 | 3/2018 | Singh Alvarado et al. |
| 9,924,893 B2 | 3/2018 | Schurman et al. |
| 9,924,897 B1 | 3/2018 | Abdul-Hafiz |
| 9,936,917 B2 | 4/2018 | Poeze et al. |
| 9,943,269 B2 | 4/2018 | Muhsin et al. |
| 9,949,676 B2 | 4/2018 | Al-Ali |
| 9,952,095 B1 | 4/2018 | Hotelling et al. |
| 9,955,937 B2 | 5/2018 | Telfort |
| 9,965,946 B2 | 5/2018 | Al-Ali |
| 9,980,667 B2 | 5/2018 | Kiani et al. |
| D820,865 S | 6/2018 | Muhsin et al. |
| 9,986,919 B2 | 6/2018 | Lamego et al. |
| 9,986,952 B2 | 6/2018 | Dalvi et al. |
| 9,989,560 B2 | 6/2018 | Poeze et al. |
| 9,993,207 B2 | 6/2018 | Al-Ali et al. |
| 10,007,758 B2 | 6/2018 | Al-Ali et al. |
| D822,215 S | 7/2018 | Al-Ali et al. |
| D822,216 S | 7/2018 | Barker et al. |
| 10,010,276 B2 | 7/2018 | Al-Ali et al. |
| 10,032,002 B2 | 7/2018 | Kiani et al. |
| 10,039,080 B2 | 7/2018 | Miller et al. |
| 10,039,482 B2 | 8/2018 | Al-Ali et al. |
| 10,039,491 B2 | 8/2018 | Thompson et al. |
| 10,052,037 B2 | 8/2018 | Kinast et al. |
| 10,055,121 B2 | 8/2018 | Chaudhri et al. |
| 10,058,275 B2 | 8/2018 | Al-Ali et al. |
| 10,064,562 B2 | 9/2018 | Al-Ali |
| 10,066,970 B2 | 9/2018 | Gowreesunker et al. |
| 10,076,257 B2 | 9/2018 | Lin et al. |
| 10,078,052 B2 | 9/2018 | Ness et al. |
| 10,086,138 B1 | 10/2018 | Novak, Jr. |
| 10,092,200 B2 | 10/2018 | Al-Ali et al. |
| 10,092,244 B2 | 10/2018 | Chuang et al. |
| 10,092,249 B2 | 10/2018 | Kiani et al. |
| 10,098,550 B2 | 10/2018 | Al-Ali et al. |
| 10,098,591 B2 | 10/2018 | Al-Ali et al. |
| 10,098,610 B2 | 10/2018 | Al-Ali et al. |
| D833,624 S | 11/2018 | DeJong et al. |
| 10,117,587 B2 | 11/2018 | Han |
| 10,123,726 B2 | 11/2018 | Al-Ali et al. |
| 10,130,289 B2 | 11/2018 | Al-Ali et al. |
| 10,130,291 B2 | 11/2018 | Schurman et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,165,954 B2 | 1/2019 | Lee |
| 10,188,296 B2 | 1/2019 | Al-Ali et al. |
| 10,188,331 B1 | 1/2019 | Al-Ali et al. |
| 10,188,348 B2 | 1/2019 | Kiani et al. |
| RE47,218 E | 2/2019 | Al-Ali |
| RE47,244 E | 2/2019 | Kiani et al. |
| RE47,249 E | 2/2019 | Kiani et al. |
| 10,194,847 B2 | 2/2019 | Al-Ali |
| 10,194,848 B1 | 2/2019 | Kiani et al. |
| 10,201,286 B2 | 2/2019 | Waydo |
| 10,201,298 B2 | 2/2019 | Al-Ali et al. |
| 10,205,272 B2 | 2/2019 | Kiani et al. |

(56) References Cited

U.S. PATENT DOCUMENTS

| | | |
|---|---|---|
| 10,205,291 B2 | 2/2019 | Scruggs et al. |
| 10,213,108 B2 | 2/2019 | Al-Ali |
| 10,215,698 B2 | 2/2019 | Han et al. |
| 10,219,706 B2 | 3/2019 | Al-Ali |
| 10,219,746 B2 | 3/2019 | McHale et al. |
| 10,219,754 B1 | 3/2019 | Lamego |
| 10,226,187 B2 | 3/2019 | Al-Ali et al. |
| 10,226,576 B2 | 3/2019 | Kiani |
| 10,231,657 B2 | 3/2019 | Al-Ali et al. |
| 10,231,670 B2 | 3/2019 | Blank et al. |
| 10,231,676 B2 | 3/2019 | Al-Ali et al. |
| RE47,353 E | 4/2019 | Kiani et al. |
| 10,247,670 B2 | 4/2019 | Ness et al. |
| 10,251,585 B2 | 4/2019 | Al-Ali et al. |
| 10,251,586 B2 | 4/2019 | Lamego |
| 10,255,994 B2 | 4/2019 | Sampath et al. |
| 10,258,265 B1 | 4/2019 | Poeze et al. |
| 10,258,266 B1 | 4/2019 | Poeze et al. |
| 10,265,024 B2 | 4/2019 | Lee et al. |
| 10,271,748 B2 | 4/2019 | Al-Ali |
| 10,278,626 B2 | 5/2019 | Schurman et al. |
| 10,278,648 B2 | 5/2019 | Al-Ali et al. |
| 10,279,247 B2 | 5/2019 | Kiani |
| 10,285,626 B1 | 5/2019 | Kestelli et al. |
| 10,292,628 B1 | 5/2019 | Poeze et al. |
| 10,292,657 B2 | 5/2019 | Abdul-Hafiz et al. |
| 10,292,664 B2 | 5/2019 | Al-Ali |
| 10,299,708 B1 | 5/2019 | Poeze et al. |
| 10,299,709 B2 | 5/2019 | Perea et al. |
| 10,305,775 B2 | 5/2019 | Lamego et al. |
| 10,307,111 B2 | 6/2019 | Muhsin et al. |
| 10,325,681 B2 | 6/2019 | Sampath et al. |
| 10,327,337 B2 | 6/2019 | Triman et al. |
| 10,390,716 B2 | 8/2019 | Shimuta |
| 10,398,383 B2 | 9/2019 | van Dinther et al. |
| 10,406,445 B2 | 9/2019 | Vock et al. |
| 10,416,079 B2 | 9/2019 | Magnussen et al. |
| 2002/0042558 A1 | 4/2002 | Mendelson |
| 2003/0036690 A1 | 2/2003 | Geddes et al. |
| 2004/0054290 A1 | 3/2004 | Chance |
| 2004/0114783 A1 | 6/2004 | Spycher et al. |
| 2005/0277819 A1 | 12/2005 | Kiani et al. |
| 2006/0009607 A1 | 1/2006 | Lutz et al. |
| 2006/0161054 A1 | 7/2006 | Reuss et al. |
| 2006/0182659 A1* | 8/2006 | Unlu ............... G01N 21/0303 422/82.05 |
| 2007/0282478 A1 | 12/2007 | Al-Ali et al. |
| 2008/0030468 A1 | 2/2008 | Al-Ali et al. |
| 2009/0177097 A1 | 7/2009 | Ma et al. |
| 2009/0247984 A1 | 10/2009 | Lamego et al. |
| 2009/0275813 A1 | 11/2009 | Davis |
| 2009/0275844 A1 | 11/2009 | Al-Ali |
| 2010/0004518 A1 | 1/2010 | Vo et al. |
| 2010/0030040 A1 | 2/2010 | Poeze et al. |
| 2010/0030043 A1 | 2/2010 | Kuhn |
| 2010/0113948 A1 | 5/2010 | Yang et al. |
| 2011/0004106 A1 | 1/2011 | Iwamiya et al. |
| 2011/0082711 A1 | 4/2011 | Poeze et al. |
| 2011/0085721 A1 | 4/2011 | Guyon et al. |
| 2011/0105854 A1 | 5/2011 | Kiani et al. |
| 2011/0125060 A1 | 5/2011 | Telfort et al. |
| 2011/0208015 A1 | 8/2011 | Welch et al. |
| 2011/0213212 A1 | 9/2011 | Al-Ali |
| 2011/0230733 A1 | 9/2011 | Al-Ali |
| 2011/0237969 A1 | 9/2011 | Eckerbom et al. |
| 2011/0245697 A1 | 10/2011 | Miettinen |
| 2011/0288383 A1 | 11/2011 | Diab |
| 2011/0301444 A1 | 12/2011 | Al-Ali |
| 2012/0041316 A1 | 2/2012 | Al-Ali et al. |
| 2012/0046557 A1 | 2/2012 | Kiani |
| 2012/0059267 A1 | 3/2012 | Lamego et al. |
| 2012/0088984 A1 | 4/2012 | Al-Ali et al. |
| 2012/0150052 A1 | 6/2012 | Buchheim et al. |
| 2012/0165629 A1 | 6/2012 | Merritt et al. |
| 2012/0179006 A1 | 7/2012 | Jansen et al. |
| 2012/0197093 A1 | 8/2012 | LeBoeuf et al. |
| 2012/0197137 A1 | 8/2012 | Jeanne et al. |
| 2012/0209082 A1 | 8/2012 | Al-Ali |
| 2012/0209084 A1 | 8/2012 | Olsen et al. |
| 2012/0283524 A1 | 11/2012 | Kiani et al. |
| 2012/0296178 A1 | 11/2012 | Lamego et al. |
| 2012/0319816 A1 | 12/2012 | Al-Ali |
| 2012/0330112 A1 | 12/2012 | Lamego et al. |
| 2013/0006076 A1 | 1/2013 | McHale |
| 2013/0018233 A1 | 1/2013 | Cinbis et al. |
| 2013/0023775 A1 | 1/2013 | Lamego et al. |
| 2013/0041591 A1 | 2/2013 | Lamego |
| 2013/0046204 A1 | 2/2013 | Lamego et al. |
| 2013/0060147 A1 | 3/2013 | Welch et al. |
| 2013/0085346 A1 | 4/2013 | Lin et al. |
| 2013/0096405 A1 | 4/2013 | Garfio |
| 2013/0096936 A1 | 4/2013 | Sampath et al. |
| 2013/0131474 A1 | 5/2013 | Gu et al. |
| 2013/0190581 A1 | 7/2013 | Al-Ali et al. |
| 2013/0204112 A1* | 8/2013 | White ............... A61B 5/0261 600/407 |
| 2013/0211214 A1 | 8/2013 | Olsen |
| 2013/0243021 A1 | 9/2013 | Siskavich |
| 2013/0253334 A1 | 9/2013 | Al-Ali et al. |
| 2013/0262730 A1 | 10/2013 | Al-Ali et al. |
| 2013/0267804 A1 | 10/2013 | Al-Ali |
| 2013/0274572 A1 | 10/2013 | Al-Ali et al. |
| 2013/0296672 A1 | 11/2013 | O'Neil et al. |
| 2013/0296713 A1 | 11/2013 | Al-Ali et al. |
| 2013/0317370 A1 | 11/2013 | Dalvi et al. |
| 2013/0324808 A1 | 12/2013 | Al-Ali et al. |
| 2013/0331660 A1 | 12/2013 | Al-Ali et al. |
| 2013/0331670 A1 | 12/2013 | Kiani |
| 2014/0012100 A1 | 1/2014 | Al-Ali et al. |
| 2014/0034353 A1 | 2/2014 | Al-Ali et al. |
| 2014/0051953 A1 | 2/2014 | Lamego et al. |
| 2014/0051955 A1 | 2/2014 | Tiao et al. |
| 2014/0066783 A1 | 3/2014 | Kiani et al. |
| 2014/0073887 A1 | 3/2014 | Petersen et al. |
| 2014/0073960 A1 | 3/2014 | Rodriguez-Llorente et al. |
| 2014/0077956 A1 | 3/2014 | Sampath et al. |
| 2014/0081100 A1 | 3/2014 | Muhsin et al. |
| 2014/0081175 A1 | 3/2014 | Telfort |
| 2014/0094667 A1 | 4/2014 | Schurman et al. |
| 2014/0100434 A1 | 4/2014 | Diab et al. |
| 2014/0107493 A1 | 4/2014 | Yuen et al. |
| 2014/0114199 A1 | 4/2014 | Lamego et al. |
| 2014/0120564 A1 | 5/2014 | Workman et al. |
| 2014/0121482 A1 | 5/2014 | Merritt et al. |
| 2014/0121483 A1 | 5/2014 | Kiani |
| 2014/0127137 A1 | 5/2014 | Bellott et al. |
| 2014/0129702 A1 | 5/2014 | Lamego et al. |
| 2014/0135588 A1 | 5/2014 | Al-Ali et al. |
| 2014/0142401 A1 | 5/2014 | Al-Ali et al. |
| 2014/0163344 A1 | 6/2014 | Al-Ali |
| 2014/0163402 A1 | 6/2014 | Lamego et al. |
| 2014/0166076 A1 | 6/2014 | Kiani et al. |
| 2014/0171146 A1 | 6/2014 | Ma et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0180160 A1 | 6/2014 | Brown et al. |
| 2014/0187973 A1 | 7/2014 | Brown et al. |
| 2014/0192177 A1 | 7/2014 | Bartula et al. |
| 2014/0194766 A1 | 7/2014 | Al-Ali et al. |
| 2014/0206954 A1 | 7/2014 | Yuen et al. |
| 2014/0206963 A1 | 7/2014 | Al-Ali |
| 2014/0213864 A1 | 7/2014 | Abdul-Hafiz et al. |
| 2014/0221854 A1 | 8/2014 | Wai |
| 2014/0266790 A1 | 9/2014 | Al-Ali et al. |
| 2014/0275808 A1 | 9/2014 | Poeze et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0275881 A1 | 9/2014 | Lamego et al. |
| 2014/0276013 A1 | 9/2014 | Muehlemann et al. |
| 2014/0276115 A1 | 9/2014 | Dalvi et al. |
| 2014/0276116 A1 | 9/2014 | Takahashi et al. |
| 2014/0288400 A1 | 9/2014 | Diab et al. |

(56) References Cited

U.S. PATENT DOCUMENTS

| | | |
|---|---|---|
| 2014/0303520 A1 | 10/2014 | Telfort et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330092 A1 | 11/2014 | Al-Ali et al. |
| 2014/0330098 A1 | 11/2014 | Merritt et al. |
| 2014/0330099 A1 | 11/2014 | Al-Ali et al. |
| 2014/0336481 A1 | 11/2014 | Shakespeare et al. |
| 2014/0357966 A1 | 12/2014 | Al-Ali et al. |
| 2014/0361147 A1* | 12/2014 | Fei .................. G01J 1/0407 250/206 |
| 2014/0371548 A1 | 12/2014 | Al-Ali et al. |
| 2014/0371632 A1 | 12/2014 | Al-Ali et al. |
| 2014/0378784 A1 | 12/2014 | Kiani et al. |
| 2014/0378844 A1 | 12/2014 | Fei |
| 2015/0005600 A1 | 1/2015 | Blank et al. |
| 2015/0011907 A1 | 1/2015 | Purdon et al. |
| 2015/0012231 A1 | 1/2015 | Poeze et al. |
| 2015/0018650 A1 | 1/2015 | Al-Ali et al. |
| 2015/0025406 A1 | 1/2015 | Al-Ali |
| 2015/0032029 A1 | 1/2015 | Al-Ali et al. |
| 2015/0038859 A1 | 2/2015 | Dalvi et al. |
| 2015/0045637 A1 | 2/2015 | Dalvi |
| 2015/0045685 A1 | 2/2015 | Al-Ali et al. |
| 2015/0051462 A1 | 2/2015 | Olsen |
| 2015/0065889 A1 | 3/2015 | Gandelman et al. |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0097701 A1 | 4/2015 | Al-Ali et al. |
| 2015/0099324 A1 | 4/2015 | Wojtczuk et al. |
| 2015/0099950 A1 | 4/2015 | Al-Ali et al. |
| 2015/0099951 A1 | 4/2015 | Al-Ali et al. |
| 2015/0099955 A1 | 4/2015 | Al-Ali et al. |
| 2015/0101844 A1 | 4/2015 | Al-Ali et al. |
| 2015/0106121 A1 | 4/2015 | Muhsin et al. |
| 2015/0112151 A1 | 4/2015 | Muhsin et al. |
| 2015/0116076 A1 | 4/2015 | Al-Ali et al. |
| 2015/0119725 A1 | 4/2015 | Martin et al. |
| 2015/0126830 A1 | 5/2015 | Schurman et al. |
| 2015/0133755 A1 | 5/2015 | Smith et al. |
| 2015/0140863 A1 | 5/2015 | Al-Ali et al. |
| 2015/0141781 A1 | 5/2015 | Weber et al. |
| 2015/0165312 A1 | 6/2015 | Kiani |
| 2015/0173671 A1 | 6/2015 | Paalasmaa et al. |
| 2015/0196237 A1 | 7/2015 | Lamego |
| 2015/0201874 A1 | 7/2015 | Diab |
| 2015/0208966 A1 | 7/2015 | Al-Ali |
| 2015/0216459 A1 | 8/2015 | Al-Ali et al. |
| 2015/0230755 A1 | 8/2015 | Al-Ali et al. |
| 2015/0238722 A1 | 8/2015 | Al-Ali |
| 2015/0245773 A1 | 9/2015 | Lamego et al. |
| 2015/0245793 A1 | 9/2015 | Al-Ali et al. |
| 2015/0245794 A1 | 9/2015 | Al-Ali |
| 2015/0255001 A1 | 9/2015 | Haughav et al. |
| 2015/0257689 A1 | 9/2015 | Al-Ali et al. |
| 2015/0272514 A1 | 10/2015 | Kiani et al. |
| 2015/0281424 A1 | 10/2015 | Vock et al. |
| 2015/0318100 A1 | 11/2015 | Rothkopf et al. |
| 2015/0351697 A1 | 12/2015 | Weber et al. |
| 2015/0351704 A1 | 12/2015 | Kiani et al. |
| 2015/0359429 A1 | 12/2015 | Al-Ali et al. |
| 2015/0366472 A1 | 12/2015 | Kiani |
| 2015/0366507 A1 | 12/2015 | Blank |
| 2015/0374298 A1 | 12/2015 | Al-Ali et al. |
| 2015/0380875 A1 | 12/2015 | Coverston et al. |
| 2016/0000362 A1 | 1/2016 | Diab et al. |
| 2016/0007930 A1 | 1/2016 | Weber et al. |
| 2016/0019360 A1 | 1/2016 | Pahwa et al. |
| 2016/0022160 A1 | 1/2016 | Pi et al. |
| 2016/0023245 A1 | 1/2016 | Zadesky et al. |
| 2016/0029932 A1 | 2/2016 | Al-Ali |
| 2016/0029933 A1 | 2/2016 | Al-Ali et al. |
| 2016/0038045 A1 | 2/2016 | Shapiro |
| 2016/0041531 A1 | 2/2016 | Mackie et al. |
| 2016/0045118 A1 | 2/2016 | Kiani |
| 2016/0051157 A1 | 2/2016 | Waydo |
| 2016/0051158 A1 | 2/2016 | Silva |
| 2016/0051205 A1 | 2/2016 | Al-Ali et al. |
| 2016/0058302 A1 | 3/2016 | Raghuram et al. |
| 2016/0058309 A1 | 3/2016 | Han |
| 2016/0058310 A1 | 3/2016 | Iijima |
| 2016/0058312 A1 | 3/2016 | Han et al. |
| 2016/0058338 A1 | 3/2016 | Schurman et al. |
| 2016/0058347 A1 | 3/2016 | Reichgott et al. |
| 2016/0058356 A1 | 3/2016 | Raghuram et al. |
| 2016/0058370 A1 | 3/2016 | Raghuram et al. |
| 2016/0066823 A1 | 3/2016 | Kind et al. |
| 2016/0066824 A1 | 3/2016 | Al-Ali et al. |
| 2016/0066879 A1 | 3/2016 | Telfort et al. |
| 2016/0071392 A1 | 3/2016 | Hankey et al. |
| 2016/0072429 A1 | 3/2016 | Kiani et al. |
| 2016/0073967 A1 | 3/2016 | Lamego et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0106367 A1 | 4/2016 | Jorov et al. |
| 2016/0113527 A1 | 4/2016 | Al-Ali et al. |
| 2016/0143548 A1 | 5/2016 | Al-Ali |
| 2016/0154950 A1 | 6/2016 | Nakajima et al. |
| 2016/0157780 A1 | 6/2016 | Rimminen et al. |
| 2016/0166182 A1 | 6/2016 | Al-Ali et al. |
| 2016/0166183 A1 | 6/2016 | Poeze et al. |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0213309 A1 | 7/2016 | Sannholm et al. |
| 2016/0228043 A1 | 8/2016 | O'Neil et al. |
| 2016/0233632 A1 | 8/2016 | Scruggs et al. |
| 2016/0234944 A1 | 8/2016 | Schmidt et al. |
| 2016/0256058 A1 | 9/2016 | Pham et al. |
| 2016/0256082 A1 | 9/2016 | Ely et al. |
| 2016/0267238 A1 | 9/2016 | Nag |
| 2016/0270735 A1 | 9/2016 | Diab et al. |
| 2016/0283665 A1 | 9/2016 | Sampath et al. |
| 2016/0287090 A1 | 10/2016 | Al-Ali et al. |
| 2016/0287107 A1 | 10/2016 | Szabados et al. |
| 2016/0287181 A1 | 10/2016 | Han et al. |
| 2016/0287786 A1 | 10/2016 | Kiani |
| 2016/0296169 A1 | 10/2016 | McHale et al. |
| 2016/0296173 A1 | 10/2016 | Culbert |
| 2016/0296174 A1 | 10/2016 | Isikman et al. |
| 2016/0310027 A1 | 10/2016 | Han |
| 2016/0310052 A1 | 10/2016 | Al-Ali et al. |
| 2016/0314260 A1 | 10/2016 | Kiani |
| 2016/0324488 A1 | 11/2016 | Olsen |
| 2016/0327984 A1 | 11/2016 | Al-Ali et al. |
| 2016/0331332 A1 | 11/2016 | Al-Ali |
| 2016/0367173 A1 | 12/2016 | Dalvi et al. |
| 2016/0378069 A1 | 12/2016 | Rothkopf |
| 2016/0378071 A1 | 12/2016 | Rothkopf |
| 2017/0000394 A1 | 1/2017 | Al-Ali et al. |
| 2017/0007134 A1 | 1/2017 | Al-Ali et al. |
| 2017/0007183 A1 | 1/2017 | Dusan et al. |
| 2017/0007198 A1 | 1/2017 | Al-Ali et al. |
| 2017/0010858 A1 | 1/2017 | Prest et al. |
| 2017/0014083 A1 | 1/2017 | Diab et al. |
| 2017/0014084 A1 | 1/2017 | Al-Ali et al. |
| 2017/0024748 A1 | 1/2017 | Haider |
| 2017/0042488 A1 | 2/2017 | Muhsin |
| 2017/0055851 A1 | 3/2017 | Al-Ali |
| 2017/0055882 A1 | 3/2017 | Al-Ali et al. |
| 2017/0055887 A1 | 3/2017 | Al-Ali |
| 2017/0055896 A1 | 3/2017 | Al-Ali et al. |
| 2017/0074897 A1 | 3/2017 | Mermel et al. |
| 2017/0079594 A1 | 3/2017 | Telfort et al. |
| 2017/0084133 A1 | 3/2017 | Cardinali et al. |
| 2017/0086689 A1 | 3/2017 | Shui et al. |
| 2017/0086723 A1 | 3/2017 | Al-Ali et al. |
| 2017/0086742 A1 | 3/2017 | Harrison-Noonan et al. |

(56) References Cited

U.S. PATENT DOCUMENTS

| | | |
|---|---|---|
| 2017/0086743 A1 | 3/2017 | Bushnell et al. |
| 2017/0094450 A1 | 3/2017 | Tu et al. |
| 2017/0143281 A1 | 5/2017 | Olsen |
| 2017/0147774 A1 | 5/2017 | Kiani |
| 2017/0156620 A1 | 6/2017 | Al-Ali et al. |
| 2017/0164884 A1 | 6/2017 | Culbert et al. |
| 2017/0172435 A1 | 6/2017 | Presura |
| 2017/0172476 A1 | 6/2017 | Schilthuizen |
| 2017/0173632 A1 | 6/2017 | Al-Ali |
| 2017/0187146 A1 | 6/2017 | Kiani et al. |
| 2017/0188919 A1 | 7/2017 | Al-Ali et al. |
| 2017/0196464 A1 | 7/2017 | Jansen et al. |
| 2017/0196470 A1 | 7/2017 | Lamego et al. |
| 2017/0202505 A1 | 7/2017 | Kirenko et al. |
| 2017/0209095 A1 | 7/2017 | Wagner et al. |
| 2017/0224262 A1 | 8/2017 | Al-Ali |
| 2017/0228516 A1 | 8/2017 | Sampath et al. |
| 2017/0245790 A1 | 8/2017 | Al-Ali et al. |
| 2017/0248446 A1 | 8/2017 | Gowreesunker et al. |
| 2017/0251974 A1 | 9/2017 | Shreim et al. |
| 2017/0251975 A1 | 9/2017 | Shreim et al. |
| 2017/0258403 A1 | 9/2017 | Abdul-Hafiz et al. |
| 2017/0273619 A1 | 9/2017 | Alvarado et al. |
| 2017/0281024 A1 | 10/2017 | Narasimhan et al. |
| 2017/0293727 A1 | 10/2017 | Klaassen et al. |
| 2017/0311851 A1 | 11/2017 | Schurman et al. |
| 2017/0311891 A1 | 11/2017 | Kiani et al. |
| 2017/0325698 A1 | 11/2017 | Allec et al. |
| 2017/0325728 A1 | 11/2017 | Al-Ali et al. |
| 2017/0325744 A1 | 11/2017 | Allec et al. |
| 2017/0332976 A1 | 11/2017 | Al-Ali et al. |
| 2017/0340209 A1 | 11/2017 | Klaassen et al. |
| 2017/0340219 A1 | 11/2017 | Sullivan et al. |
| 2017/0340293 A1 | 11/2017 | Al-Ali et al. |
| 2017/0347885 A1 | 12/2017 | Tan et al. |
| 2017/0354332 A1 | 12/2017 | Lamego |
| 2017/0354795 A1 | 12/2017 | Blahnik et al. |
| 2017/0358239 A1 | 12/2017 | Arney et al. |
| 2017/0358240 A1 | 12/2017 | Blahnik et al. |
| 2017/0358242 A1 | 12/2017 | Thompson et al. |
| 2017/0360306 A1 | 12/2017 | Narasimhan et al. |
| 2017/0360310 A1 | 12/2017 | Kiani et al. |
| 2017/0366657 A1 | 12/2017 | Thompson et al. |
| 2017/0367632 A1 | 12/2017 | Al-Ali et al. |
| 2018/0008146 A1 | 1/2018 | Al-Ali et al. |
| 2018/0013562 A1 | 1/2018 | Haider et al. |
| 2018/0014752 A1 | 1/2018 | Al-Ali et al. |
| 2018/0014781 A1 | 1/2018 | Clavelle et al. |
| 2018/0025287 A1 | 1/2018 | Mathew et al. |
| 2018/0056129 A1 | 1/2018 | Narasimha Rao et al. |
| 2018/0028124 A1 | 2/2018 | Al-Ali et al. |
| 2018/0042556 A1 | 2/2018 | Shahparnia et al. |
| 2018/0049694 A1 | 2/2018 | Singh Alvarado et al. |
| 2018/0050235 A1 | 2/2018 | Tan et al. |
| 2018/0055375 A1 | 3/2018 | Martinez et al. |
| 2018/0055385 A1 | 3/2018 | Al-Ali |
| 2018/0055390 A1 | 3/2018 | Kiani et al. |
| 2018/0055430 A1 | 3/2018 | Diab et al. |
| 2018/0055439 A1 | 3/2018 | Pham et al. |
| 2018/0064381 A1 | 3/2018 | Shakespeare et al. |
| 2018/0069776 A1 | 3/2018 | Lamego et al. |
| 2018/0070867 A1 | 3/2018 | Smith et al. |
| 2018/0078151 A1 | 3/2018 | Allec et al. |
| 2018/0078182 A1 | 3/2018 | Chen et al. |
| 2018/0082767 A1 | 3/2018 | Al-Ali et al. |
| 2018/0085068 A1 | 3/2018 | Telfort |
| 2018/0087937 A1 | 3/2018 | Al-Ali et al. |
| 2018/0103874 A1 | 4/2018 | Lee et al. |
| 2018/0103905 A1 | 4/2018 | Kiani |
| 2018/0110469 A1 | 4/2018 | Maani et al. |
| 2018/0110478 A1 | 4/2018 | Al-Ali |
| 2018/0116575 A1 | 5/2018 | Perea et al. |
| 2018/0125368 A1 | 5/2018 | Lamego et al. |
| 2018/0125430 A1 | 5/2018 | Al-Ali et al. |
| 2018/0125445 A1 | 5/2018 | Telfort et al. |
| 2018/0130325 A1 | 5/2018 | Kiani et al. |
| 2018/0132769 A1 | 5/2018 | Weber et al. |
| 2018/0132770 A1 | 5/2018 | Lamego |
| 2018/0146901 A1 | 5/2018 | Al-Ali et al. |
| 2018/0146902 A1 | 5/2018 | Kiani et al. |
| 2018/0153418 A1 | 6/2018 | Sullivan et al. |
| 2018/0153442 A1 | 6/2018 | Eckerbom et al. |
| 2018/0153446 A1 | 6/2018 | Kiani |
| 2018/0153447 A1 | 6/2018 | Al-Ali et al. |
| 2018/0153448 A1 | 6/2018 | Weber et al. |
| 2018/0161499 A1 | 6/2018 | Al-Ali et al. |
| 2018/0164853 A1 | 6/2018 | Myers et al. |
| 2018/0168491 A1 | 6/2018 | Al-Ali et al. |
| 2018/0174679 A1 | 6/2018 | Sampath et al. |
| 2018/0174680 A1 | 6/2018 | Sampath et al. |
| 2018/0182484 A1 | 6/2018 | Sampath et al. |
| 2018/0184917 A1 | 7/2018 | Kiani |
| 2018/0192924 A1 | 7/2018 | Al-Ali |
| 2018/0192953 A1 | 7/2018 | Shreim et al. |
| 2018/0192955 A1 | 7/2018 | Al-Ali et al. |
| 2018/0196514 A1 | 7/2018 | Allec et al. |
| 2018/0199871 A1 | 7/2018 | Pauley et al. |
| 2018/0206795 A1 | 7/2018 | Al-Ali |
| 2018/0206815 A1 | 7/2018 | Telfort |
| 2018/0213583 A1 | 7/2018 | Al-Ali |
| 2018/0214031 A1 | 8/2018 | Kiani et al. |
| 2018/0214090 A1 | 8/2018 | Al-Ali et al. |
| 2018/0218792 A1 | 8/2018 | Muhsin et al. |
| 2018/0225960 A1 | 8/2018 | Al-Ali et al. |
| 2018/0228414 A1 | 8/2018 | Shao et al. |
| 2018/0238718 A1 | 8/2018 | Dalvi |
| 2018/0238734 A1 | 8/2018 | Hotelling et al. |
| 2018/0242853 A1 | 8/2018 | Al-Ali |
| 2018/0242921 A1 | 8/2018 | Muhsin et al. |
| 2018/0242923 A1 | 8/2018 | Al-Ali et al. |
| 2018/0242924 A1 | 8/2018 | Barker et al. |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0249933 A1 | 9/2018 | Schurman et al. |
| 2018/0253947 A1 | 9/2018 | Muhsin et al. |
| 2018/0256087 A1 | 9/2018 | Al-Ali et al. |
| 2018/0256113 A1 | 9/2018 | Weber et al. |
| 2018/0279956 A1 | 10/2018 | Waydo et al. |
| 2018/0285094 A1 | 10/2018 | Housel et al. |
| 2018/0289325 A1 | 10/2018 | Poeze et al. |
| 2018/0289337 A1 | 10/2018 | Al-Ali et al. |
| 2018/0296161 A1 | 10/2018 | Shreim et al. |
| 2018/0300919 A1 | 10/2018 | Muhsin et al. |
| 2018/0310822 A1 | 11/2018 | Indorf et al. |
| 2018/0310823 A1 | 11/2018 | Al-Ali et al. |
| 2018/0317826 A1 | 11/2018 | Muhsin |
| 2018/0317841 A1 | 11/2018 | Novak, Jr. |
| 2018/0333055 A1 | 11/2018 | Lamego et al. |
| 2018/0333087 A1 | 11/2018 | Al-Ali |
| 2019/0000317 A1 | 1/2019 | Muhsin et al. |
| 2019/0000362 A1 | 1/2019 | Kiani et al. |
| 2019/0015023 A1 | 1/2019 | Monfre |
| 2019/0021638 A1 | 1/2019 | Al-Ali et al. |
| 2019/0029574 A1 | 1/2019 | Schurman et al. |
| 2019/0029578 A1 | 1/2019 | Al-Ali et al. |
| 2019/0038143 A1 | 2/2019 | Al-Ali |
| 2019/0058280 A1 | 2/2019 | Al-Ali et al. |
| 2019/0058281 A1 | 2/2019 | Al-Ali et al. |
| 2019/0069813 A1 | 3/2019 | Al-Ali |
| 2019/0069814 A1 | 3/2019 | Al-Ali |
| 2019/0076028 A1 | 3/2019 | Al-Ali et al. |
| 2019/0082979 A1 | 3/2019 | Al-Ali et al. |
| 2019/0090748 A1 | 3/2019 | Al-Ali |
| 2019/0090760 A1 | 3/2019 | Kinast et al. |
| 2019/0090764 A1 | 3/2019 | Al-Ali |
| 2019/0104973 A1 | 4/2019 | Poeze et al. |
| 2019/0110719 A1 | 4/2019 | Poeze et al. |
| 2019/0117070 A1 | 4/2019 | Muhsin et al. |
| 2019/0117139 A1 | 4/2019 | Al-Ali et al. |
| 2019/0117140 A1 | 4/2019 | Al-Ali et al. |
| 2019/0117141 A1 | 4/2019 | Al-Ali |
| 2019/0117930 A1 | 4/2019 | Al-Ali |
| 2019/0122763 A1 | 4/2019 | Sampath et al. |

(56) References Cited

U.S. PATENT DOCUMENTS

| | | |
|---|---|---|
| 2019/0133525 A1 | 5/2019 | Al-Ali et al. |
| 2019/0142283 A1 | 5/2019 | Lamego et al. |
| 2019/0142344 A1 | 5/2019 | Telfort et al. |
| 2019/0150800 A1 | 5/2019 | Poeze et al. |
| 2019/0150856 A1 | 5/2019 | Kiani et al. |
| 2019/0167161 A1 | 6/2019 | Al-Ali et al. |
| 2019/0175019 A1 | 6/2019 | Al-Ali et al. |
| 2019/0192076 A1 | 6/2019 | McHale et al. |

FOREIGN PATENT DOCUMENTS

| | | |
|---|---|---|
| CN | 103906468 A | 7/2014 |
| EP | 0630208 A1 | 12/1994 |
| EP | 0770349 A1 | 5/1997 |
| EP | 0781527 A1 | 7/1997 |
| EP | 0880936 A2 | 12/1998 |
| EP | 0985373 A1 | 3/2000 |
| EP | 1124609 B1 | 8/2001 |
| EP | 2277440 A1 | 1/2011 |
| GB | 2243691 A | 11/1991 |
| JP | H09257508 A | 10/1997 |
| JP | H10314133 A | 12/1998 |
| JP | H1170086 A | 3/1999 |
| JP | 2919326 B2 | 7/1999 |
| KR | 2010/0091592 A | 8/2010 |
| KR | 20100091592 A | 8/2010 |
| WO | WO 1994/23643 A1 | 10/1994 |
| WO | WO 1995/000070 A1 | 1/1995 |
| WO | WO 1995000070 A1 | 1/1995 |
| WO | WO 1996/027325 A1 | 9/1996 |
| WO | WO 1997/00923 A1 | 1/1997 |
| WO | WO 1997009923 A1 | 3/1997 |
| WO | WO 1996/063883 A1 | 12/1999 |
| WO | WO 1999063883 A1 | 12/1999 |
| WO | WO 2000/028892 A1 | 5/2000 |
| WO | WO 2000028892 A1 | 5/2000 |
| WO | WO 02/028274 | 4/2002 |
| WO | WO 2006/113070 | 10/2006 |
| WO | WO 2008/107238 A1 | 9/2008 |
| WO | WO 2009/001988 | 12/2008 |
| WO | WO 2009/137524 | 11/2009 |
| WO | WO 2011/069122 | 6/2011 |
| WO | WO 2013/030744 A1 | 3/2013 |
| WO | WO 2013030744 A1 | 3/2013 |
| WO | WO 2013/106607 A1 | 7/2013 |
| WO | WO 2013/181368 | 12/2013 |
| WO | WO 2014/18447 A1 | 1/2014 |
| WO | WO 2014/115075 A1 | 7/2014 |
| WO | WO 2014/153200 A1 | 9/2014 |
| WO | WO 2014/178793 | 11/2014 |
| WO | WO 2014184447 A1 | 11/2014 |
| WO | WO 2015/187732 A1 | 12/2015 |
| WO | WO 2016/066312 | 5/2016 |

OTHER PUBLICATIONS

Konig, V. et al., "Reflectance Pulse Oximetry—Principles and Obstetric Application in the Zurich System," J Clin Monit 1998; 14: 403-412.

Written Opinion received in International Application No. PCT/US2016/040190, dated Jan. 2, 2018.

Anliker et al., "AMON: A wearable multiparameter medical monitoring and alert system," in *IEEE Transactions on Information Technology in Biomedicine*, vol. 8, No. 4, Dec. 2004.

Lukowicz, et al. "AMON: A wearable medical computer for high risk patients," *Proceedings. Sixth International Symposium on Wearable Computers*, 2002.

Jan. 9, 2020 Complaint for (1) Patent Infringement (2) Trade Secret Misappropriation and (3) Ownership of Patents and Demand for Jury Trial, *Masimo Corporation and Cercacor Laboratories, Inc.* v. *Apple Inc.*, Case No. 8:20-cv-00048, 64 pages.

Asada, et al. "Mobile Monitoring with Wearable Photoplethysmographic Biosensors", IEEE Engineering in Medicine and Biology Magazine, 2003.

Bagha, et al. "A Real Time Analysis of PPG Signal for Measurement of SpO2 and Pulse Rate", International Journal of Computer Applications (0975-8887), vol. 36— No. 11, 2011.

Branche, et al. "Measurement Reproducibility and Sensor Placement Considerations in Designing a Wearable Pulse Oximeter for Military Applications", IEEE, 2004.

Branche, et al. "Signal Quality and Power Consumption of a New Prototype Reflectance Pulse Oximeter Sensor", IEEE, 2005.

Celka, et al. "Motion resistant earphone located infrared based heart rate measurement device", Research Gate, 2004.

Comtois, et al. "A Comparative Evaluation of Adaptive Noise Cancellation Algorithms for Minimizing Motion Artifacts in a Forehead-Mounted Wearable Pulse Oximeter", IEEE, 2007.

Comtois, et al. "A Noise Reference Input to an Adaptive Filter Algorithm for Signal Processing in a Wearable Pulse Oximeter", IEEE, 2007.

Crilly, et al. "An Integrated Pulse Oximeter System for Telemedicine Applications", IEEE Instrumentation and Measurement Technology Conference, 1997.

Dassel, et al. "Reflective Pulse Oximetry at the Forehead Improves by Pressure on the Probe", J. Clin. Monit, 11:237-244, 1995.

Dresher, et al. "A New Reflectance Pulse Oximeter Housing to Reduce Contact Pressure Effects", IEEE, 2006.

Dresher, et al. "Reflectance Forehead Pulse Oximetry: Effects of Contact Pressure During Walking", IEEE, 2006.

Gibbs, et al. "Active motion artifact cancellation for wearable health monitoring sensors using collocated MEMS accelerometers", SPIE, vol. 5765, 2005.

Johnston, et al. "Extracting Breathing Rate Information from a Wearable Reflectance Pulse Oximeter Sensor", IEEE, 2004.

Johnston, et al. "Extracting Heart Rate Variability From a Wearable Reflectance Pulse Oximeter", IEEE, 2005.

Konstantas, et al. "Mobile Patient Monitoring: The MobiHealth System", Research Gate, 2004.

Lee, et al. "Development of a Wristwatch-Type PPG Array Sensor Module", IEEE, 2011.

Lin, et al. "RTWPMS: A Real-Time Wireless Physiological Monitoring System", IEEE Transactions on Information Technology in Biomedicine, vol. 10, No. 4, 2006.

Lingaiah, et al. "Measurement of Pulse rate and SPo2 using Pulse Oximeter developed using LabVIEW", IOSR Journal of Electrical and Electronics Engineering (IOSR-JEEE), e-ISSN: 2278-1676,p-ISSN: 2320-3331, vol. 8, Issue 1, pp. 22-26, 2013.

Lukowicz, et al. "The Weararm Modular, Low-Power Computing Core", IEEE Micro, 2001.

Mapar "Wearable Sensor for Continuously Cigilant Blood Perfusion and Oxygenation", UCLA, 2012.

Mendelson et al. "Noninvasive Pulse Oximetry Utilizing Skin Reflectance Photoplethysmography", IEEE Biomedical Engineering, vol. 35 No. 10, 1988.

Mendelson et al., "A Mobile PDA-Based Wireless Pulse Oximeter," Proceedings of the IASTED International Conference Telehealth, Jul. 19-21, 2005, pp. 1-6.

Mendelson et al., "A Wearable Reflectance Pulse Oximeter for Remote Physiological Monitoring," Proceedings of the 28th IEEE EMBS Annual International Conference, Aug. 30-Sep. 3, 2006, pp. 912-915.

Mendelson et al., "Accelerometery-Based Adaptive Noise Cancellation for Remote Physiological Monitoring by a Wearable Pulse Oximeter," Proceedings of the 3rd IASTED International Conference TELEHEALTH, May 31-Jun. 1, 2007, pp. 28-33.

Mendelson et al., "Measurement Site and Photodetector Size Considerations in Optimizing Power Consumption of a Wearable Reflectance Pulse Oximeter," Proceedings of the 25th Annual International Conference of the IEEE EMBS, Sep. 17-21, 2003, pp. 3016-3019.

Mendelson et al., "Minimization of LED Power Consumption in the Design of a Wearable Pulse Oximeter,"Proceedings of the IASTED International Conference Biomedical Engineering, Jun. 25-27, 2003, 6 pages.

(56) References Cited

OTHER PUBLICATIONS

Oliver et al., "HealthGear: A Real-time Wearable System for Monitoring and Analyzing Physiological Signals," Proceedings of the International Workshop on Wearable and Implantable Body Sensor Networks, IEEE Computer Society, 2006, pp. 1-4.
Pandian et al., "Smart Vest: Wearable Multi-Parameter Remote Physiological Monitoring System," Medical Engineering & Physics 30, 2008. pp. 466-477.
Poh et al. "Motion-Tolerant Magnetic Earring Sensor and Wireless Earpiece for Wearable Photoplethysmography", IEEE Transactions on Information Technology in Biomedicine, vol. 14, No. 3, 2010.
Purjary et al., "Photodetector Size Considerations in the Design of a Noninvasive Reflectance Pulse Oximeter for Telemedicine Applications", IEEE, 2003.
Renevey et al., "Wrist-Located Pulse Detection Using IR Signals, Activity and Nonlinear Artifact Cancellation," Proceedings of the 23rd Annual EMBS International Conference, Oct. 25-28, 2001, pp. 3030-3033.
Rhee et al. "Artifact-Resistant Power-Efficient Design of Finger-Ring Plethysmographic Sensors," IEEE Transactions on Biomedical Engineering, vol. 48, No. 7, Jul. 2001, pp. 795-805.
Rhee et al. "Artifact-Resistant, Power Efficient Design of Finger-Ring Plethysmographic Sensors, Part I: Design and Analysis," 22nd Annual International Conference IEEE Engineering in Medicine and Biology Society, Jul. 23-28, 2000, pp. 2792-2795.
Rhee et al., "Design of a Artifact-Free Wearable Plethysmographic Sensor," 21st Annual International Conferemce IEEE Engineering in Medicine and Biology Society, Oct. 13-16, 1999, p. 786.
Rhee et al., "The Ring Sensor: a New Ambulatory Wearable Sensor for Twenty-Four Hour Patient Monitoring," Proceedings of the 20th Annual International Conference of the IEEE Engineering in Medicine and Biology Society, Oct. 29-Nov. 1, 1998, 4 pages.
Savage et al., "Optimizing Power Consumption in the Design of a Wearable Wireless Telesensor: Comparison of Pulse Oximeter Modes," Proceedings of IEEE 29th Annual Nonheust Bioengineering Conference, 2003, pp. 150-151.
Scully, et al. "Physiological Parameter Monitoring from Optical Recordings with a Mobile Phone", IEEE Trans Biomed Eng. ; 59(2): 303-306, 2012.
Shaltis et al., "Novel Design for a Wearable, Rapidly Depolyable, Wireless Noninvasive Triage Sensor," Proceedings of the 2005 IEEE, Engineering in Medicine and Biology 27th Annual Conference, Sep. 1-4, 2005, pp. 3567-3570.
Shin et al., "A Novel Headset with a Transmissive PPG Sensor for Heart Rate Measurement", ICBME 2008, Proceedings 23, pp. 519-522, 2009.
Stojanovic, et al. "Design of an Oximeter Based on LED-LED Configuration and FPGA Technology", Sensors, 13, 574-586, 2013.
Stuban, et al. "Optimal filter bandwidth for pulse oximetry", Rev. Sci. Instrum. 83, 104708, 2012.
Tamannagari, "Power Efficient Design of Finder-Ring Sensor for Patient Monitoring," Master of Science in Electrical Engineering, The University of Texas at San Antonio, College of Engineering, Department of Electrical Engineering, Dec. 2008, 74 pages.
Tamura et al. "Wearable Photoplethysmographic Sensors—Past and Present", Electronics, 3, 282-302, 2014.
Tofs, et al. "Body-Heat Powered Autonomous Pulse Oximeter", IEEE Sensors, 2006.
Townsend, et al. "Pulse Oximetry", Medical Electronics, 2001.
Tura, et al., "A Medical Wearable Device with Wireless Bluetooth-based Data Transmission", Measurement Science Review, vol. 3, Section 2, 2003.
Vogel, et al. "In-Ear Vital Signs Monitoring Using a Novel Microoptic Reflective Sensor", IEEE Transactions on Information Technology in Biomedicine, vol. 13, No. 6, 2009.
Yamashita et al., "Development of a Ring-Type Vital Sign Telemeter," Biotelemetry XIII, Mar. 26-31, 1995, pp. 145-150.
Yan, et al. "An Efficient Motion-Resistant Method for Wearable Pulse Oximeter", IEEE Transactions on Information Technology in Biomedicine, vol. 12, No. 3, 2008.
Yang, et al. "A Twenty-Four Hour Tele-Nursing System Using a Ring Sensor", Proc. of 1998 Int. Conf. on Robotics and Automation, 1998.
Yang, et al. "SpO2 and Heart Rate Measurement with Wearable Watch Based on PPG", IEEE, 2015.
Zhai, et al. "A Wireless Sensor Network for Hospital Patient Monitoring", University of Calgary, 2007.
Conway, et al. "Wearable computer as a multi-parametric monitor for physiological signals," Proceedings IEEE International Symposium on Bio-Informatics and Biomedical Engineering, pp. 236-242, 2000.
Keikhosravi, et al. "Effect of deep breath on the correlation between the wrist and finger photoplethysmograms", pp. 135-138, 2012.
Kuboyama, "Motion Artifact Cancellation for Wearable Photoplethysmographic Sensor", Massachusetts Institute of Technology, pp. 1-66, 2010.
Phattraprayoon, et al. "Accuracy of Pulse Oximeter Readings From Probe Placementon Newborn Wrist and Ankle", Journal of Perinatology, vol. 32, pp. 276-280, 2012.
Pujary, "Investigation of Photodetector Optimization in Reducing Power Consumption by a Noninvasive Pulse Oximeter Sensor", Worcester Polytechnic Institute, pp. 1-133, 2004.
Shyamkumar, et al. "Wearable Wireless Cardiovascular Monitoring Using Textile-Based Nanosensor and Nanomaterial Systems", Electronics 3, pp. 504-520, 2014.
Warren, et al. "Designing Smart Health Care Technology into the Home of the Future", United States: N. p., 1999.
Yang, et al. "Development of the Ring Sensor for Healthcare Automation", Robotics and Autonomous Systems, 30, pp. 273-281, 2000.
"Heart Rate Measurement Technology" EPSON, 2019.
"Introducing Easy Pulse: A DIY Photoplethysmographic Sensor for Measuring Heart Rate", Embedded Lab, 2012.
"PerformTek Precision Biometrics", ValenCell, 2013.
"Galaxy S5 Explained: the Heart Rate Sensor and S Health 3.0." Samsung Global Newsroom, 2014.
"Withings Pulse: Activity Tracker—Sleep Analyzer Hear Rate Analyzer; Installation and Operating Instructions", Withings, 2015.
Faulkner, "Apple Watch Heart Rate Sensor: Everything You Need to Know." TechRadar India, TechRadar, 2015.
Hayes, "How the Sensors inside Fitness Tracker Work." Digital Trends, 2014.
Heerlein, et al. "LED-Based Sensor for Wearable Fitness Tracking Products", EDN, 2014.
Kilbane, et al. "Design Considerations for Wrist-Wearable Heart Rate Monitors," Arrow Intelligent Systems, 2015.
Kviesis-Kipge, et al., "Miniature Wireless Photoplethysmography Devices: Integration in Garments and Test Measurements", SPIE vol. 8427 84273H-6, 2012.

\* cited by examiner

PHYSIOLOGICAL MONITORING DEVICES, SYSTEMS, AND METHODS

INCORPORATION BY REFERENCE TO ANY PRIORITY APPLICATIONS

The present application is a continuation of U.S. patent application Ser. No. 16/226,249 filed Dec. 19, 2018, which is a continuation of U.S. patent application Ser. No. 15/195,199 filed Jun. 28, 2016, which claims priority benefit under 35 U.S.C. § 119(e) from U.S. Provisional Application No. 62/188,430, filed Jul. 2, 2015, entitled "Advanced Pulse Oximetry Sensor," which is incorporated by reference herein. Any and all applications for which a foreign or domestic priority claim is identified in the Application Data Sheet as filed with the present application are hereby incorporated by reference under 37 CFR 1.57.

FIELD OF THE DISCLOSURE

The present disclosure relates to the field of non-invasive optical-based physiological monitoring sensors, and more particularly to systems, devices and methods for improving the non-invasive measurement accuracy of oxygen saturation, among other physiological parameters.

BACKGROUND

Spectroscopy is a common technique for measuring the concentration of organic and some inorganic constituents of a solution. The theoretical basis of this technique is the Beer-Lambert law, which states that the concentration $c_i$ of an absorbent in solution can be determined by the intensity of light transmitted through the solution, knowing the pathlength $d_\lambda$, the intensity of the incident light $I_{0,\lambda}$, and the extinction coefficient $\varepsilon_{i,\lambda}$ at a particular wavelength $\lambda$.

In generalized form, the Beer-Lambert law is expressed as:

$$I_\lambda = I_{0,\lambda} e^{-d_\lambda \cdot \mu_{a,\lambda}} \quad (1)$$

$$\mu_{a,\lambda} = \sum_{i=1}^{n} \varepsilon_{i,\lambda} \cdot c_i \quad (2)$$

where $\mu_{a,\lambda}$ is the bulk absorption coefficient and represents the probability of absorption per unit length. The minimum number of discrete wavelengths that are required to solve equations 1 and 2 is the number of significant absorbers that are present in the solution.

A practical application of this technique is pulse oximetry, which utilizes a noninvasive sensor to measure oxygen saturation and pulse rate, among other physiological parameters. Pulse oximetry relies on a sensor attached externally to the patient to output signals indicative of various physiological parameters, such as a patient's blood constituents and/or analytes, including for example a percent value for arterial oxygen saturation, among other physiological parameters. The sensor has an emitter that transmits optical radiation of one or more wavelengths into a tissue site and a detector that responds to the intensity of the optical radiation after absorption by pulsatile arterial blood flowing within the tissue site. Based upon this response, a processor determines the relative concentrations of oxygenated hemoglobin ($HbO_2$) and deoxygenated hemoglobin (Hb) in the blood so as to derive oxygen saturation, which can provide early detection of potentially hazardous decreases in a patient's oxygen supply.

A pulse oximetry system generally includes a patient monitor, a communications medium such as a cable, and/or a physiological sensor having one or more light emitters and a detector, such as one or more light-emitting diodes (LEDs) and a photodetector. The sensor is attached to a tissue site, such as a finger, toe, earlobe, nose, hand, foot, or other site having pulsatile blood flow which can be penetrated by light from the one or more emitters. The detector is responsive to the emitted light after attenuation or reflection by pulsatile blood flowing in the tissue site. The detector outputs a detector signal to the monitor over the communication medium. The monitor processes the signal to provide a numerical readout of physiological parameters such as oxygen saturation (SpO2) and/or pulse rate. A pulse oximetry sensor is described in U.S. Pat. No. 6,088,607 entitled Low Noise Optical Probe; pulse oximetry signal processing is described in U.S. Pat. Nos. 6,650,917 and 6,699,194 entitled Signal Processing Apparatus and Signal Processing Apparatus and Method, respectively; a pulse oximeter monitor is described in U.S. Pat. No. 6,584,336 entitled Universal/Upgrading Pulse Oximeter; all of which are assigned to Masimo Corporation, Irvine, Calif., and each is incorporated by reference herein in its entirety.

There are many sources of measurement error introduced to pulse oximetry systems. Some such sources of error include the pulse oximetry system's electronic components, including emitters and detectors, as well as chemical and structural physiological differences between patients. Another source of measurement error is the effect of multiple scattering of photons as the photons pass through the patient's tissue (arterial blood) and arrive at the sensor's light detector.

SUMMARY

This disclosure describes embodiments of non-invasive methods, devices, and systems for measuring blood constituents, analytes, and/or substances such as, by way of non-limiting example, oxygen, carboxyhemoglobin, methemoglobin, total hemoglobin, glucose, proteins, lipids, a percentage thereof (e.g., saturation), pulse rate, perfusion index, oxygen content, total hemoglobin, Oxygen Reserve Index™ (ORI™) or for measuring many other physiologically relevant patient characteristics. These characteristics can relate to, for example, pulse rate, hydration, trending information and analysis, and the like.

In an embodiment, an optical physiological measurement system includes an emitter configured to emit light of one or more wavelengths. The system also includes a diffuser configured to receive the emitted light, to spread the received light, and to emit the spread light over a larger tissue area than would otherwise be penetrated by the emitter directly emitting light at a tissue measurement site. The tissue measurement site can include, such as, for example, a finger, a wrist, or the like. The system further includes a concentrator configured to receive the spread light after it has been attenuated by or reflected from the tissue measurement site. The concentrator is also configured to collect and concentrate the received light and to emit the concentrated light to a detector. The detector is configured to detect the concentrated light and to transmit a signal indicative of the detected light. The system also includes a processor configured to receive the transmitted signal indicative of the detected light and to determine, based on an amount of absorption, an analyte of interest, such as, for example, arterial oxygen saturation or other parameter, in the tissue measurement site.

In certain embodiments of the present disclosure, the diffuser comprises glass, ground glass, glass beads, opal glass, or a microlens-based, band-limited, engineered diffuser that can deliver efficient and uniform illumination. In some embodiments the diffuser is further configured to define a surface area shape by which the emitted spread light is distributed onto a surface of the tissue measurement site. The defined surface area shape can include, by way of non-limiting example, a shape that is substantially rectangular, square, circular, oval, or annular, among others.

According to some embodiments, the optical physiological measurement system includes an optical filter having a light-absorbing surface that faces the tissue measurement site. The optical filter also has an opening that is configured to allow the spread light, after being attenuated by the tissue measurement site, to be received by the concentrator. In an embodiment, the opening has dimensions, wherein the dimensions of the opening are similar to the defined surface area shape by which the emitted spread light is distributed onto the surface of the tissue measurement site. In an embodiment, the opening has dimensions that are larger than the defined surface area shape by which the emitted spread light is distributed onto the surface of the tissue measurement site. In other embodiments, the dimensions of the opening in the optical filter are not the same as the diffuser opening, but the dimensions are larger than the detector package.

In other embodiments of the present disclosure, the concentrator comprises glass, ground glass, glass beads, opal glass, or a compound parabolic concentrator. In some embodiments the concentrator comprises a cylindrical structure having a truncated circular conical structure on top. The truncated section is adjacent the detector. The light concentrator is structured to receive the emitted optical radiation, after reflection by the tissue measurement site, and to direct the reflected light to the detector.

In accordance with certain embodiments of the present disclosure, the processor is configured to determine an average level of the light detected by the detector. The average level of light is used to determine a physiological parameter in the tissue measurement site.

According to another embodiment, a method to determine a constituent or analyte in a patient's blood is disclosed. The method includes emitting, from an emitter, light of at least one wavelength; spreading, with a diffuser, the emitted light and emitting the spread light from the diffuser to a tissue measurement site; receiving, by a concentrator, the spread light after the spread light has been attenuated by the tissue measurement site; concentrating, by the concentrator, the received light and emitting the concentrated light from the concentrator to a detector; detecting, with the detector, the emitted concentrated light; transmitting, from the detector, a signal responsive to the detected light; receiving, by a processor, the transmitted signal responsive to the detected light; and processing, by the processor, the received signal responsive to the detected light to determine a physiological parameter.

In some embodiments, the method to determine a constituent or analyte in a patient's blood includes filtering, with a light-absorbing detector filter, scattered portions of the emitted spread light. According to an embodiment, the light-absorbing detector filter is substantially rectangular in shape and has outer dimensions in the range of approximately 1-5 cm in width and approximately 2-8 cm in length, and has an opening through which emitted light may pass, the opening having dimensions in the range of approximately 0.25-3 cm in width and approximately 1-7 cm in length. In another embodiment, the light-absorbing detector filter is substantially square in shape and has outer dimensions in the range of approximately 0.25-10 cm$^2$, and has an opening through which emitted light may pass, the opening having dimensions in the range of approximately 0.1-8 cm$^2$. In yet another embodiment, the light-absorbing detector filter is substantially rectangular in shape and has outer dimensions of approximately 3 cm in width and approximately 6 cm in length, and has an opening through which emitted light may pass, the opening having dimensions of approximately 1.5 cm in width and approximately 4 cm in length.

In still other embodiments of the method to determine a constituent or analyte in a patient's blood, spreading, with a diffuser, the emitted light and emitting the spread light from the diffuser to a tissue measurement site is performed by at least one of a glass diffuser, a ground glass diffuser, a glass bead diffuser, an opal glass diffuser, and an engineered diffuser. In some embodiments the emitted spread light is emitted with a substantially uniform intensity profile. And in some embodiments, emitting the spread light from the diffuser to the tissue measurement site includes spreading the emitted light so as to define a surface area shape by which the emitted spread light is distributed onto a surface of the tissue measurement site.

According to yet another embodiment, a pulse oximeter is disclosed. The pulse oximeter includes an emitter configured to emit light at one or more wavelengths. The pulse oximeter also includes a diffuser configured to receive the emitted light, to spread the received light, and to emit the spread light directed at a tissue measurement sight. The pulse oximeter also includes a detector configured to detect the emitted spread light after being attenuated by or reflected from the tissue measurement site and to transmit a signal indicative of the detected light. The pulse oximeter also includes a processor configured to receive the transmitted signal and to process the received signal to determine an average absorbance of a blood constituent or analyte in the tissue measurement site over a larger measurement site area than can be performed with a point light source or point detector. In some embodiments, the diffuser is further configured to define a surface area shape by which the emitted spread light is distributed onto a surface of the tissue measurement site, and the detector is further configured to have a detection area corresponding to the defined surface area shape by which the emitted spread light is distributed onto the surface of the tissue measurement site. According to some embodiments, the detector comprises an array of detectors configured to cover the detection area. In still other embodiments, the processor is further configured to determine an average of the detected light.

For purposes of summarizing, certain aspects, advantages and novel features of the disclosure have been described herein. It is to be understood that not necessarily all such advantages can be achieved in accordance with any particular embodiment of the systems, devices and/or methods disclosed herein. Thus, the subject matter of the disclosure herein can be embodied or carried out in a manner that achieves or optimizes one advantage or group of advantages as taught herein without necessarily achieving other advantages as can be taught or suggested herein.

BRIEF DESCRIPTION OF THE DRAWINGS

Throughout the drawings, reference numbers can be reused to indicate correspondence between referenced elements. The drawings are provided to illustrate embodiments of the disclosure described herein and not to limit the scope thereof.

DETAILED DESCRIPTION

Figure 1:
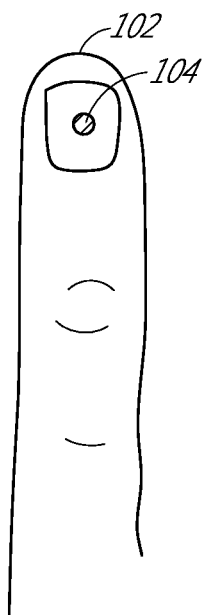
FIG. 1 illustrates a conventional approach to two-dimensional pulse oximetry in which the emitter is configured to emit optical radiation as a point optical source.

FIG. 1 illustrates schematically a conventional pulse oximetry sensor having a two-dimensional (2D) approach to pulse oximetry. As illustrated, the emitter 104 is configured to emit optical radiation as a point optical source, i.e., an optical radiation source that has negligible dimensions such that it may be considered as a point. This approach is referred to herein as "two-dimensional" pulse oximetry because it applies a two-dimensional analytical model to the three-dimensional space of the tissue measurement site 102 of the patient. Point optical sources feature a defined, freely selectable, and homogeneous light beam area. Light beams emitted from LED point sources often exhibit a strong focus which can produce a usually sharply-defined and evenly-lit illuminated spot often with high intensity dynamics. Illustratively, when looking at the surface of the tissue measurement site 102 (or "sample tissue"), which in this example is a finger, a small point-like surface area of tissue 204 is irradiated by a point optical source. In some embodiments, the irradiated circular area of the point optical source is in the range between 8 and 150 microns. Illustratively, the emitted point optical source of light enters the tissue measurement site 102 as a point of light. As the light penetrates the depth of the tissue 102, it does so as a line or vector, representing a two-dimensional construct within a three-dimensional structure, namely the patient's tissue 102.

Use of a point optical source is believed to reduce variability in light pathlength which would lead to more accurate oximetry measurements. However, in practice, photons do not travel in straight paths. Instead, the light particles scatter, bouncing around between various irregular objects (such as, for example, red blood cells) in the patient's blood. Accordingly, photon pathlengths vary depending on, among other things, their particular journeys through and around the tissue at the measurement site 102. This phenomenon is referred to as "multiple scattering." In a study, the effects of multiple scattering were examined by comparing the results of photon diffusion analysis with those obtained using an analysis based on the Beer-Lambert law, which neglects multiple scattering in the determination of light pathlength. The study found that that the difference between the average lengths of the paths traveled by red and infrared photons makes the oximeter's calibration curve (based on measurements obtained from normal subjects) sensitive to the total attenuation coefficients of the tissue in the two wavelength bands used for pulse oximetry, as well as to absorption by the pulsating arterial blood.

Figure 2:
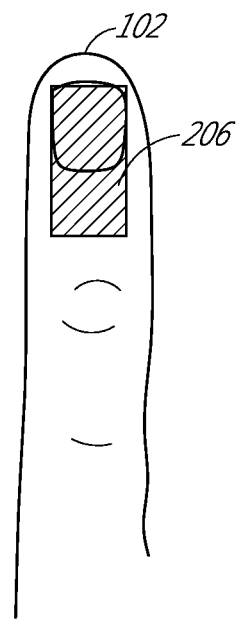
FIG. 2 illustrates the disclosed three-dimensional approach to pulse oximetry in which the emitted light irradiates a substantially larger volume of tissue as compared to the point source approach described with respect to FIG. 1.

FIG. 2 illustrates schematically the disclosed systems, devices, and methods to implement three-dimensional (3D) pulse oximetry in which the emitted light irradiates a larger volume of tissue at the measurement site 102 as compared to the 2D point optical source approach described with respect to FIG. 1. In an embodiment, again looking at the surface of the tissue measurement site 102, the irradiated surface area 206 of the measurement site 102 is substantially rectangular in shape with dimensions in the range of approximately 0.25-3 cm in width and approximately 1-6 cm in length. In another embodiment, the irradiated surface area 206 of the measurement site 102 is substantially rectangular in shape and has dimensions of approximately 1.5 cm in width and approximately 2 cm in length. In another embodiment, the irradiated surface area 206 of the measurement site 102 is substantially rectangular in shape and has dimensions of approximately 0.5 cm in width and approximately 1 cm in length. In another embodiment, the irradiated surface area 206 of the measurement site 102 is substantially rectangular in shape has dimensions of approximately 1 cm in width and approximately 1.5 cm in length. In yet another embodiment, the irradiated surface area 206 of the measurement site 102 is substantially square in shape and has dimensions in a range of approximately 0.25-9 $cm^2$. In certain embodiments, the irradiated surface area 206 of the measurement site 102 is within a range of approximately 0.5-2 cm in width, and approximately 1-4 cm in length. Of course a skilled artisan will appreciate that many other shapes and dimensions of irradiated surface area 206 can be used. Advantageously, by irradiating the tissue measurement site 102 with a surface area 206, the presently disclosed systems, devices, and methods apply a three-dimensional analytical model to the three-dimensional structure being measured, namely, the patient's sample tissue 102.

According to the Beer-Lambert law, the amount of light absorbed by a substance is proportional to the concentration of the light-absorbing substance in the irradiated solution (i.e., arterial blood). Advantageously, by irradiating a larger volume of tissue 102, a larger sample size of light attenuated (or reflected) by the tissue 102 is measured. The larger, 3D sample provides a data set that is more representative of the complete interaction of the emitted light as it passes through the patient's blood as compared to the 2D point source approach described above with respect to FIG. 1. By taking an average of the detected light, as detected over a surface area substantially larger than a single point, the disclosed pulse oximetry systems, devices, and methods will yield a more accurate measurement of the emitted light absorbed by the tissue, which will lead to a more accurate oxygen saturation measurement.

Figure 3:
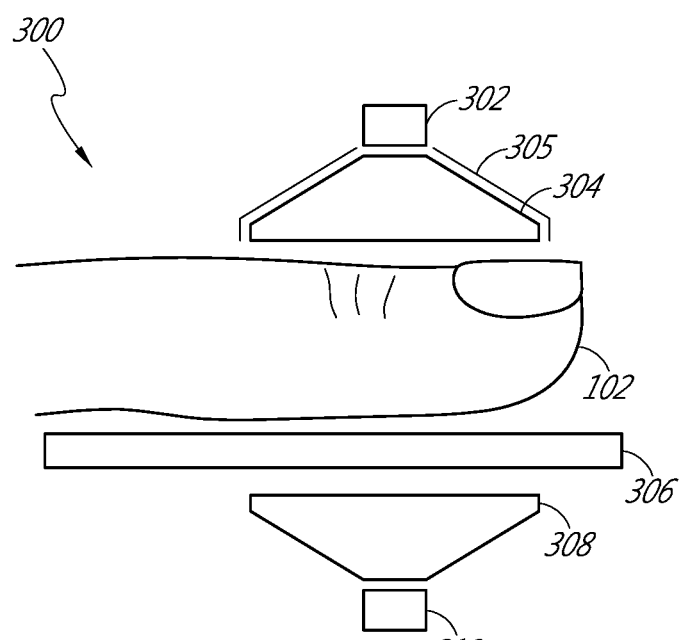
FIG. 3 illustrates schematically a side view of a three-dimensional pulse oximetry sensor according to an embodiment of the present disclosure.

FIG. 3 illustrates schematically a side view of a pulse oximetry 3D sensor 300 according to an embodiment of the present disclosure. In the illustrated embodiment, the 3D sensor 300 irradiates the tissue measurement site 102 and detects the emitted light, after being attenuated by the tissue measurement site 102. In other embodiments, for example, as describe below with respect to FIGS. 7A and 7B, the 3D sensor 300 can be arranged to detect light that is reflected by the tissue measurement site 102. The 3D sensor 300 includes an emitter 302, a light diffuser 304, a light-absorbing detector filter 306, a light concentrator 308, and a detector 310. In some optional embodiments, the 3D sensor 300 further includes a reflector 305. The reflector 305 can be a metallic reflector or other type of reflector. Reflector 305 can be a coating, film, layer or other type of reflector. The reflector 305 can serve as a reflector to prevent emitted light from emitting out of a top portion of the light diffuser 304 such that light from the emitter 302 is directed in the tissue rather than escaping out of a side or top of the light diffuser 304. Additionally, the reflector 305 can prevent ambient light from entering the diffuser 304 which might ultimately cause errors within the detected light. The reflector 305 also prevent light piping that might occur if light from the detector 302 is able to escape from the light diffuser 304 and be pipped around a sensor securement mechanism to detector 310 without passing through the patient's tissue 102.

The emitter 302 can serve as the source of optical radiation transmitted towards the tissue measurement site 102. The emitter 302 can include one or more sources of optical radiation, such as LEDs, laser diodes, incandescent bulbs with appropriate frequency-selective filters, combinations of the same, or the like. In an embodiment, the emitter 302 includes sets of optical sources that are capable of emitting visible and near-infrared optical radiation. In some embodiments, the emitter 302 transmits optical radiation of red and infrared wavelengths, at approximately 650 nm and approximately 940 nm, respectively. In some embodiments, the emitter 302 includes a single source optical radiation.

The light diffuser 304 receives the optical radiation emitted from the emitter 302 and spreads the optical radiation over an area, such as the area 206 depicted in FIG. 2. In some embodiments, the light diffuser 304 is a beam shaper that can homogenize the input light beam from the emitter 302, shape the output intensity profile of the received light, and define the way (e.g., the shape or pattern) the emitted light is distributed to the tissue measurement site 102. Examples of materials that can be used to realize the light diffuser 304 include, without limitation, a white surface, glass, ground glass, glass beads, polytetrafluoroethylene (also known as Teflon®), opal glass, and greyed glass, to name a few. Additionally, engineered diffusers can be used to realize the diffuser 304 by providing customized light shaping with respect to intensity and distribution. Such diffusers can, for example, deliver substantially uniform illumination over a specified target area (such as, for example, irradiated surface area 206) in an energy-efficient manner. Examples of engineered diffusers can include molded plastics with specific shapes, patterns or textures designed to diffuse the emitter light across the entirety of the patient's tissue surface.

Advantageously, the diffuser 304 can receive emitted light in the form of a point optical source and spread the light to fit a desired surface area on a plane defined by the surface of the tissue measurement site 102. In an embodiment, the diffuser 304 is made of ground glass which spreads the emitted light with a Gausian intensity profile. In another embodiment the diffuser 304 includes glass beads. In some embodiments, the diffuser 304 is constructed so as to diffuse the emitted light in a Lambertian pattern. A Lambertian pattern is one in which the radiation intensity is substantially constant throughout the area of dispersion. One such diffuser 304 is made from opal glass. Opal glass is similar to ground glass, but has one surface coated with a milky white coating to diffuse light evenly. In an embodiment, the diffuser 304 is capable of distributing the emitted light on the surface of a plane (e.g., the surface of the tissue measurement site 102) in a predefined geometry (e.g., a rectangle, square, or circle), and with a substantially uniform intensity profile and energy distribution. In some embodiments, the efficiency, or the amount of light transmitted by the diffuser 304, is greater than 70% of the light emitted by the emitter 302. In some embodiments, the efficiency is greater than 90% of the emitted light. Other optical elements known in the art may be used for the diffuser 304.

In an embodiment, the diffuser 304 has a substantially rectangular shape having dimensions within a range of approximately 0.5-2 cm in width and approximately 1-4 centimeters in length. In another embodiment, the substantially rectangular shape of the diffuser 304 has dimensions of approximately 0.5 cm in width and approximately 1 cm in length. In another embodiment, the diffuser's 304 substantially rectangular shape has dimensions of approximately 1 cm in width and approximately 1.5 cm in length. In yet another embodiment, the diffuser 304 has a substantially square shape with dimensions in the range of approximately 0.25-10 $cm^2$.

Figure 4A:
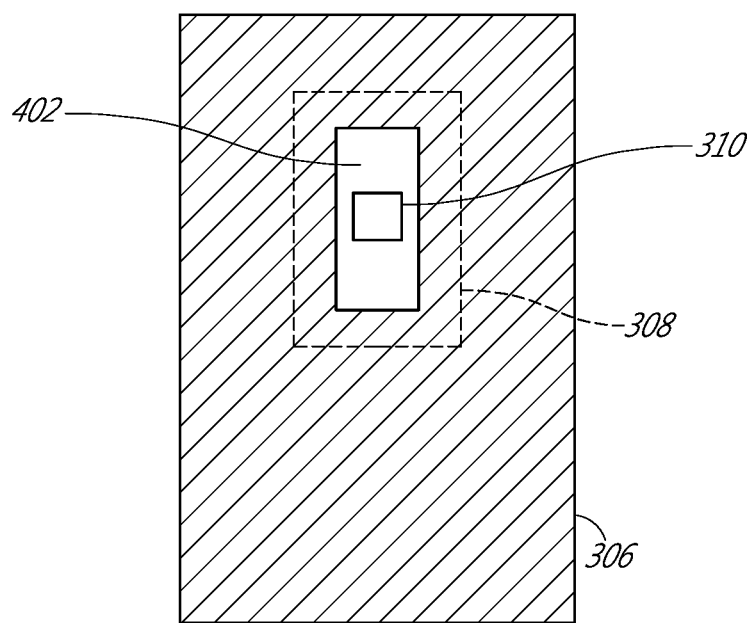
FIG. 4A is a top view of a portion of a three-dimensional pulse oximetry sensor according to an embodiment of the present disclosure.

The light-absorbing detector filter 306, which is also depicted in FIG. 4A in a top view, is a planar surface having an opening 402 through which the emitted light may pass after being attenuated by the tissue measurement site 102. In the depicted embodiment, the opening 402 is rectangular-shaped, with dimensions substantially similar to the irradiated surface area 206. According to an embodiment, the light-absorbing detector filter is substantially rectangular in shape and has outer dimensions of 4 cm in width and 8 cm in length, and has an opening through which emitted light may pass, the opening having dimensions of 2 cm in width and 5 cm in length. In another embodiment, the light-absorbing detector filter is substantially rectangular in shape and has outer dimensions in the range of 1-3 cm in width and 2-8 cm in length, and has an opening through which emitted light may pass, the opening having dimensions in the range of 0.25-2 cm in width and 1-4 cm in length. In yet another embodiment, the light-absorbing detector filter is substantially rectangular in shape and has outer dimensions of 3 cm in width and 6 cm in length, and has an opening through which emitted light may pass, the opening having dimensions of 1.5 cm in width and 4 cm in length.

The top surface of the light-absorbing filter 306 (facing the tissue measurement site 102 and the emitter 302) is coated with a material that absorbs light, such as, for example, black pigment. Many other types of light-absorbing materials are well known in the art and can be used with the detector filter 306. During operation, light emitted from the emitter 302 can reflect off of the tissue measurement site 102 (or other structures within the 3D sensor 300) to neighboring portions of the 3D sensor 300. If those neighboring portions of the 3D sensor 300 possess reflective surfaces, then the light can reflect back to the tissue measurement site 102, progress through the tissue and arrive at the detector 310. Such multiple scattering can result in detecting photons whose pathlengths are considerably longer than most of the light that is detected, thereby introducing variations in pathlength which will affect the accuracy of the measurements of the pulse oximetry 3D sensor 300. Advantageously, the light-absorbing filter 306 reduces or eliminates the amount of emitted light that is reflected in this manner because it absorbs such reflected light, thereby stopping the chain of scattering events. In certain embodiments, the sensor-facing surfaces of other portions of the 3D sensor 300 are covered in light-absorbing material to further decrease the effect of reflective multiple scattering.

The light concentrator 308 is a structure to receive the emitted optical radiation, after attenuation by the tissue measurement site 102, to collect and concentrate the dispersed optical radiation, and to direct the collected and concentrated optical radiation to the detector 310. In an embodiment, the light concentrator 308 is made of ground glass or glass beads. In some embodiments, the light concentrator 308 includes a compound parabolic concentrator.

As described above with respect to FIG. 1, the detector 310 captures and measures light from the tissue measurement site 102. For example, the detector 310 can capture and measure light transmitted from the emitter 302 that has been attenuated by the tissue in the measurement site 102. The detector 310 can output a detector signal responsive to the light captured or measured. The detector 310 can be implemented using one or more photodiodes, phototransistors, or the like. In addition, a plurality of detectors 310 can be arranged in an array with a spatial configuration corresponding to the irradiated surface area 206 to capture the attenuated or reflected light from the tissue measurement site.

Figure 4B:
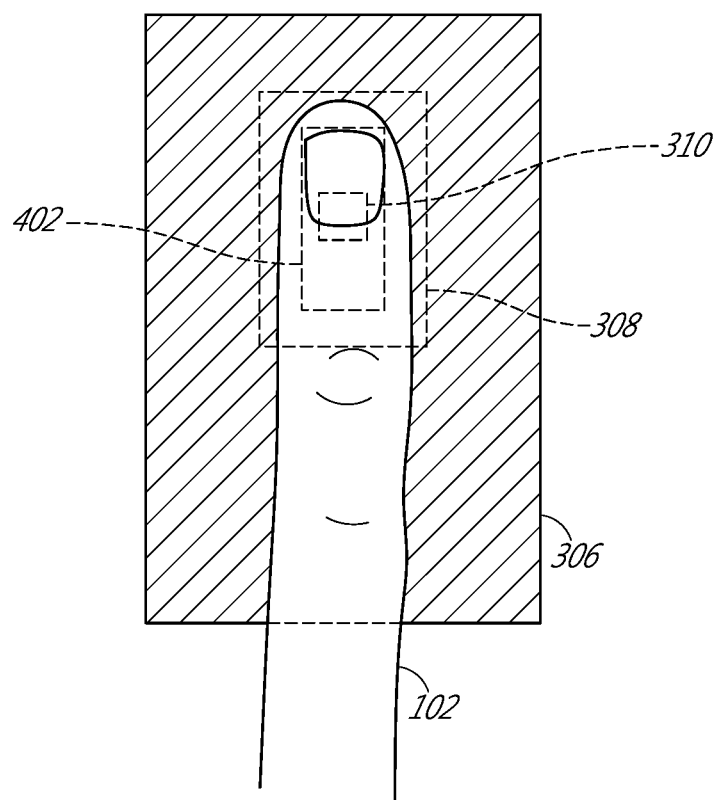
FIG. 4B illustrates the top view of a portion of the three-dimensional pulse oximetry sensor shown in FIG. 4A, with the addition of a tissue measurement site in operational position.

Referring to FIG. 4A, a top view of a portion of the 3D sensor 300 is provided. The light-absorbing detector filter 306 is illustrated having a top surface coated with a light-absorbing material. The light-absorbing material can be a black opaque material or coating or any other dark color or coating configured to absorb light. Additionally, a rectangular opening 402 is positioned relative to the light concentrator 308 (shown in phantom) and the detector 310 such that light may pass through the rectangular opening 402, into the light concentrator 308, and to the detector 310. FIG. 4B illustrates the top view of a portion of the 3D sensor 300 as in FIG. 4A, with the addition of the tissue measurement site 102 in operational position. Accordingly, the rectangular opening 402, the light concentrator 308 and the detector 310 are shown in phantom as being under the tissue measurement site 102. In FIGS. 4A and 4B, the light concentrator 308 is shown to have dimensions significantly larger than the dimensions of the rectangular opening 402. In other embodiments, the dimensions of the light concentrator 308, the rectangular opening 402, and the irradiated surface area 206 are substantially similar.

Figure 5:
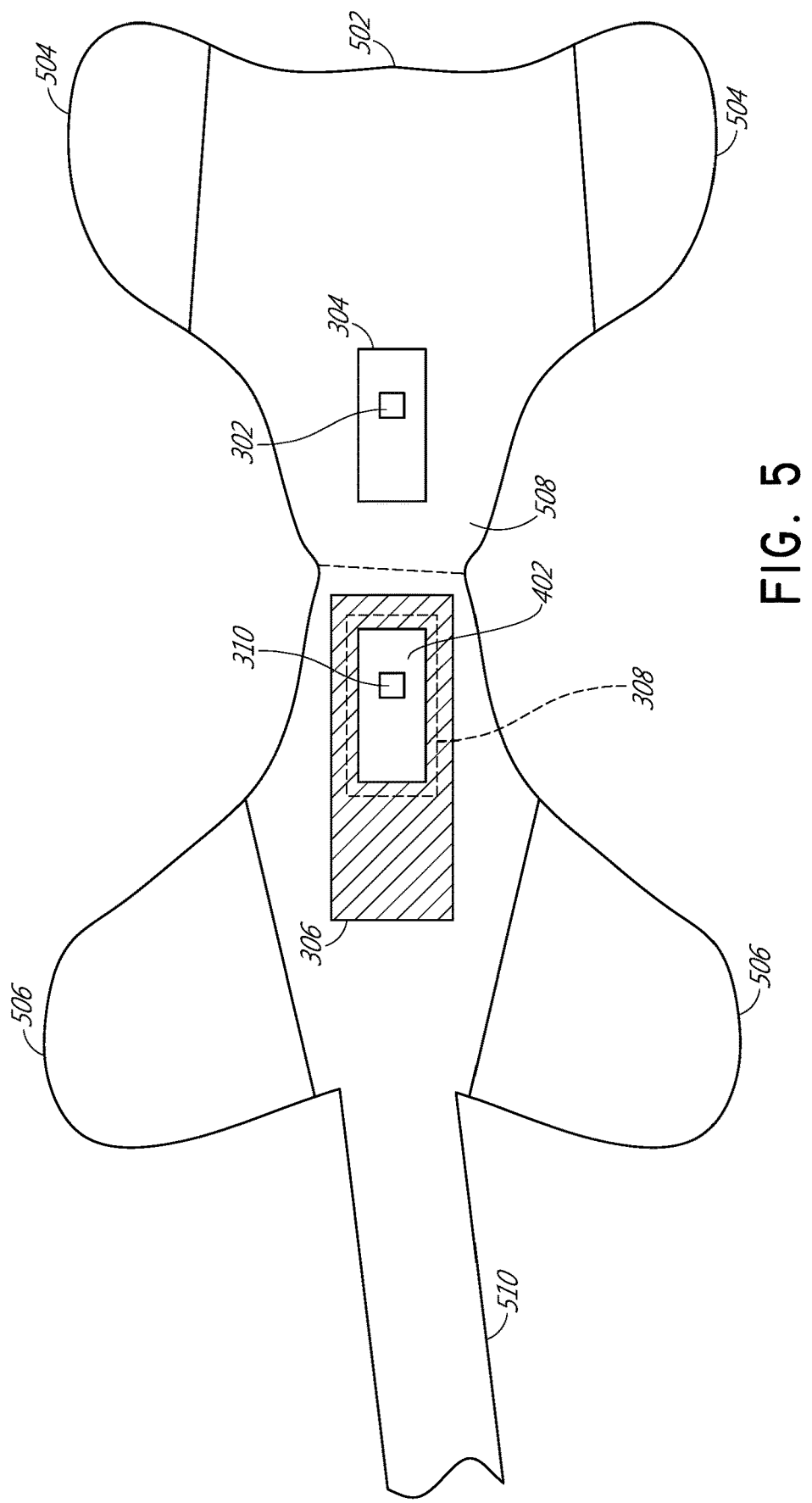
FIG. 5 illustrates a top view of a three-dimensional pulse oximetry sensor according to an embodiment of the present disclosure.

FIG. 5 illustrates a top view of a 3D pulse oximetry sensor 500 according to an embodiment of the present disclosure. The 3D sensor 500 is configured to be worn on a patient's finger 102. The 3D sensor 500 includes an adhesive substrate 502 having front flaps 504 and rear flaps 506 extending outward from a center portion 508 of the 3D sensor 500. The center portion 508 includes components of the 3D pulse oximetry sensor 300 described with respect to FIGS. 3, 4A and 4B. On the front side of the adhesive substrate 502 the emitter 302 and the light diffuser 304 are positioned. On the rear side of the adhesive substrate 502 the light-absorbent detector filter 306, the light concentrator 308 and the detector 310 are positioned. In use, the patient's finger serving as the tissue measurement site 102 is positioned over the rectangular opening 402 such that when the front portion of the adhesive substrate is folded over on top of the patient's finger 102, the emitter 302 and the light diffuser 304 are aligned with the measurement site 102, the filter 306, the light concentrator 308 and the detector 310. Once alignment is established, the front and rear flaps 504, 506 can be wrapped around the finger measurement site 102 such that the adhesive substrate 502 provides a secure contact between the patient's skin and the 3D sensor 500. FIG. 5 also illustrates an example of a sensor connector cable 510 which is used to connect the 3D sensor 500 to a monitor 809, as described with respect to FIG. 8.

Figure 6:
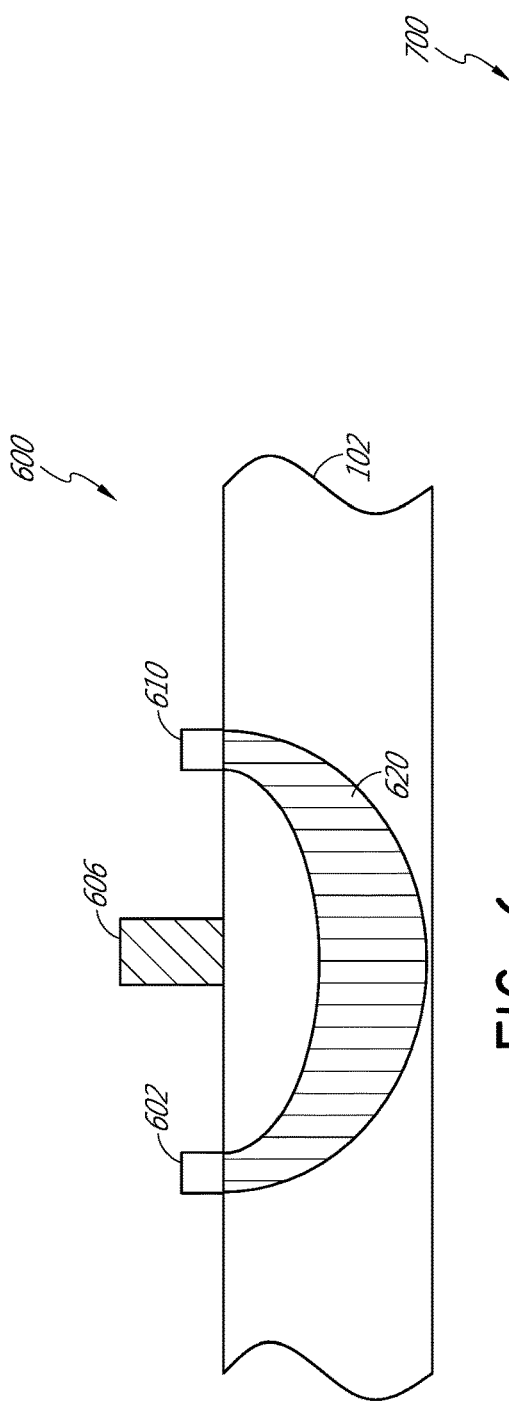
FIG. 6 illustrates a conventional two-dimensional approach to reflective pulse oximetry in which the emitter is configured to emit optical radiation as a point optical source.

FIG. 6 is a simplified schematic illustration of a conventional, 2D approach to reflective pulse oximetry in which the emitter is configured to emit optical radiation as a point optical source. Reflective pulse oximetry is a method by which the emitter and detector are located on the same side of the tissue measurement site 102. Light is emitted into a tissue measurement site 102 and attenuated. The emitted light passes into the tissue 102 and is then reflected back to the same side of the tissue measurement site 102 as the emitter. As illustrated in FIG. 6, a depicted reflective 2D pulse oximetry sensor 600 includes an emitter 602, a light block 606, and a detector 610. The light block 606 is necessary because the emitter 602 and the detector 610 are located on the same side of the tissue measurement site 102. Accordingly, the light block 606 prevents incident emitter light, which did not enter the tissue measurement site 102, from arriving at the detector 610. The depicted 2D pulse oximetry sensor 600 is configured to emit light as a point source. As depicted in FIG. 6, a simplified illustration of the light path 620 of the emitted light from the emitter 602, through the tissue measurement site 102, and to the detector 610 is provided. Notably, a point source of light is emitted, and a point source of light is detected. As discussed above with respect to FIG. 1, use of a point optical source can result in substantial measurement error due to pathlength variability resulting from the multiple scatter phenomenon. The sample space provided by a 2D point optical emitter source is not large enough to account for pathlength variability, which will skew measurement results.

Figure 7A:
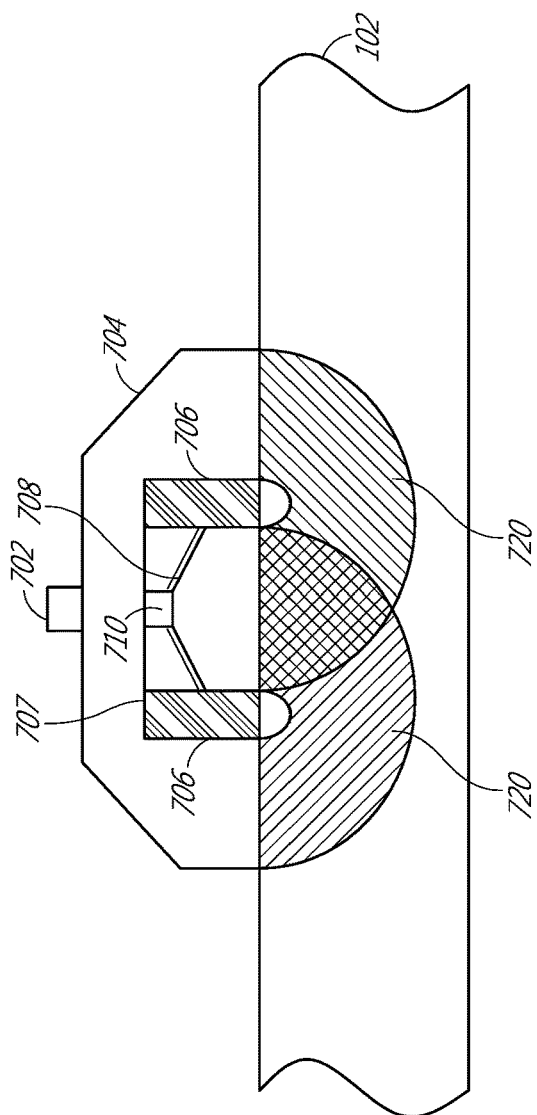
FIG. 7A is a simplified schematic side view illustration of a reflective three-dimensional pulse oximetry sensor according to an embodiment of the present disclosure.
Figure 7B:
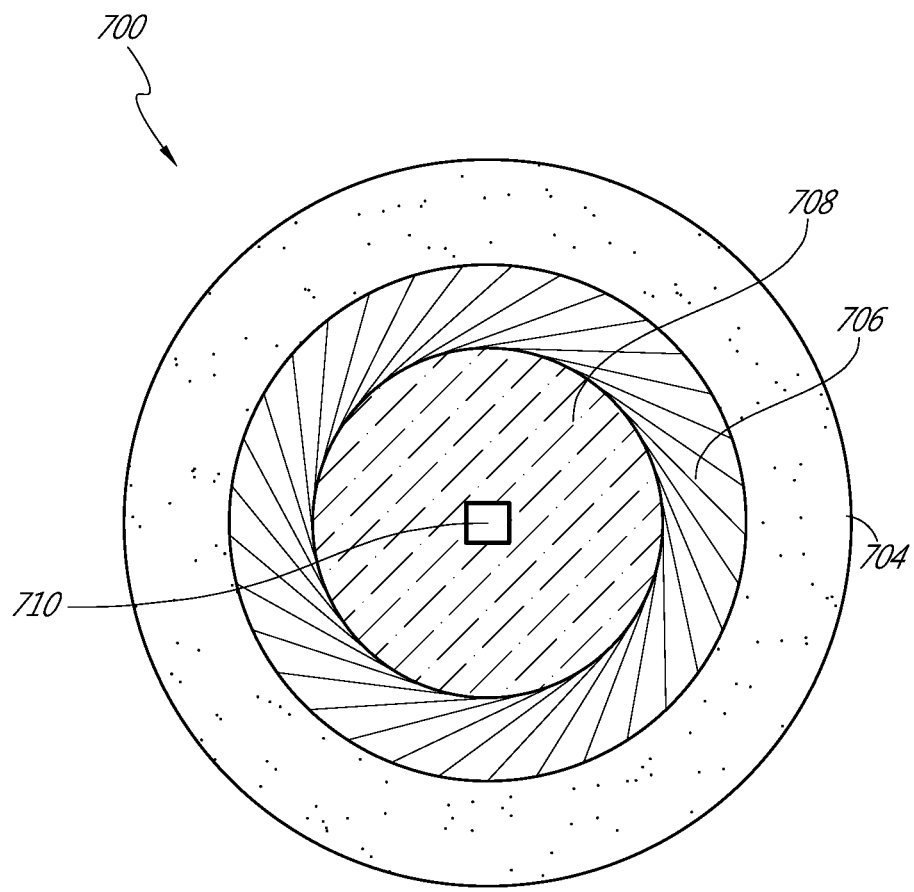
FIG. 7B is a simplified schematic top view illustration of the three-dimensional reflective pulse oximetry sensor of FIG. 7A.

FIGS. 7A and 7B are simplified schematic side and top views, respectively, of a 3D reflective pulse oximetry sensor 700 according to an embodiment of the present disclosure. In the illustrated embodiment, the 3D sensor 700 irradiates the tissue measurement site 102 and detects the emitted light that is reflected by the tissue measurement site 102. The 3D sensor 700 can be placed on a portion of the patient's body that has relatively flat surface, such as, for example a wrist, because the emitter 702 and detector 710 are on located the same side of the tissue measurement site 102. The 3D sensor 700 includes an emitter 702, a light diffuser 704, a light block 706, a light concentrator 708, and a detector 710.

As previously described, the emitter 702 can serve as the source of optical radiation transmitted towards the tissue measurement site 102. The emitter 702 can include one or more sources of optical radiation. Such sources of optical radiation can include LEDs, laser diodes, incandescent bulbs with appropriate frequency-selective filters, combinations of the same, or the like. In an embodiment, the emitter 702 includes sets of optical sources that are capable of emitting visible and near-infrared optical radiation. In some embodiments, the emitter 702 transmits optical radiation of red and infrared wavelengths, at approximately 650 nm and approximately 940 nm, respectively. In some embodiments, the emitter 702 includes a single source of optical radiation.

The light diffuser 704 receives the optical radiation emitted from the emitter 702 and homogenously spreads the optical radiation over a wide, donut-shaped area, such as the area outlined by the light diffuser 704 as depicted in FIG. 7B. Advantageously, the diffuser 704 can receive emitted light in the form of a 2D point optical source (or any other form) and spread the light to fit the desired surface area on a plane defined by the surface of the tissue measurement site 102. In an embodiment, the diffuser 704 is made of ground glass or glass beads. A skilled artisan will understand that may other materials can be used to make the light diffuser 704.

The light blocker 706 includes an annular ring having a cover portion 707 sized and shaped to form a light isolation chamber for the light concentrator 708 and the detector 710. (For purposes of illustration, the light block cover 707 is not illustrated in FIG. 7B.) The light blocker 706 and the cover 707 can be made of any material that optically isolates the light concentrator 708 and the detector 710. The light isolation chamber formed by the light blocker 706 and cover 707 ensures that the only light detected by the detector 710 is light that is reflected from the tissue measurement site.

The light concentrator 708 is a cylindrical structure with a truncated circular conical structure on top, the truncated section of which of which is adjacent the detector 710. The light concentrator 708 is structured to receive the emitted optical radiation, after reflection by the tissue measurement site 102, and to direct the reflected light to the detector 710. In an embodiment, the light concentrator 708 is made of ground glass or glass beads. In some embodiments, the light concentrator 708 includes a compound parabolic concentrator.

As previously described, the detector 710 captures and measures light from the tissue measurement site 102. For example, the detector 710 can capture and measure light transmitted from the emitter 702 that has been reflected from the tissue in the measurement site 102. The detector 710 can output a detector signal responsive to the light captured or measured. The detector 710 can be implemented using one or more photodiodes, phototransistors, or the like. In addition, a plurality of detectors 710 can be arranged in an array with a spatial configuration corresponding to the irradiated surface area depicted in FIG. 7B by the light concentrator 708 to capture the reflected light from the tissue measurement site.

Advantageously, the light path 720 illustrated in FIG. 7A depicts a substantial sample of reflected light that enter the light isolation chamber formed by the light blocker 706 and cover 707. As previously discussed, the large sample of reflected light (as compared to the reflected light collected using the 2D point optical source approach) provides the opportunity to take an average of the detected light, to derive a more accurate measurement of the emitted light absorbed by the tissue, which will lead to a more accurate oxygen saturation measurement.

Referring now to FIG. 7B, a top view of the 3D sensor 700 is illustrated with both the emitter 702 and the light blocker cover 707 removed for ease of illustration. The outer ring illustrates the footprint of the light diffuser 704. As light is emitted from the emitter 702 (not shown in FIG. 7B), it is diffused homogenously and directed to the tissue measurement site 102. The light blocker 706 forms the circular wall of a light isolation chamber to keep incident light from being sensed by the detector 710. The light blocker cover 707 blocks incidental light from entering the light isolation chamber from above. The light concentrator 708 collects the reflected light from the tissue measurement site 102 and funnels it upward toward the detector 710 at the center of the 3D sensor 700.

Figure 8:
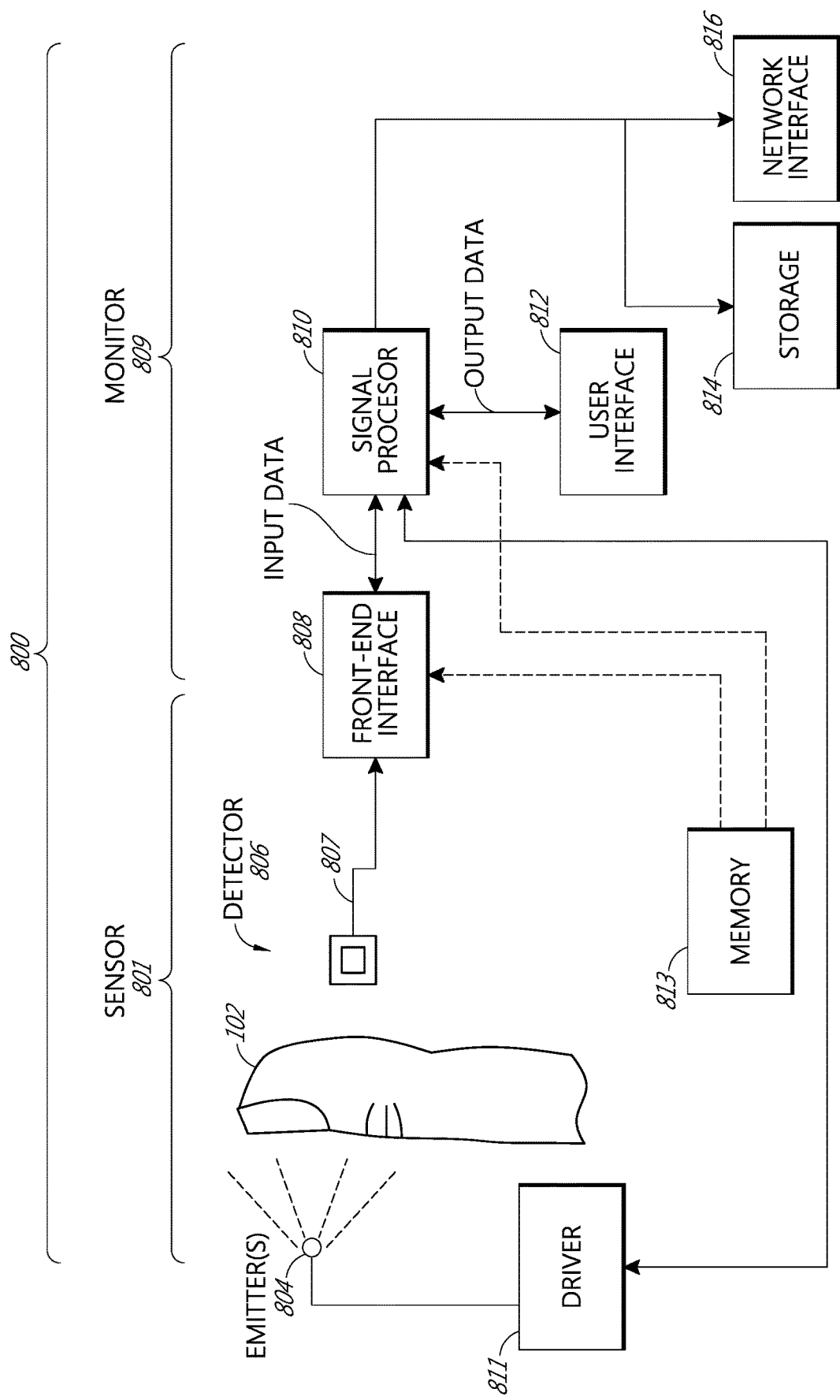
FIG. 8 illustrates a block diagram of an example pulse oximetry system capable of noninvasively measuring one or more blood analytes in a monitored patient, according to an embodiment of the disclosure.

FIG. 8 illustrates an example of an optical physiological measurement system 800, which may also be referred to herein as a pulse oximetry system 800. In certain embodiments, the pulse oximetry system 800 noninvasively measures a blood analyte, such as oxygen, carboxyhemoglobin, methemoglobin, total hemoglobin, glucose, proteins, lipids, a percentage thereof (e.g., saturation), pulse rate, perfusion index, oxygen content, total hemoglobin, Oxygen Reserve Index™ (ORI™) or many other physiologically relevant patient characteristics. These characteristics can relate to, for example, pulse rate, hydration, trending information and analysis, and the like. The system 800 can also measure additional blood analytes and/or other physiological parameters useful in determining a state or trend of wellness of a patient.

The pulse oximetry system 800 can measure analyte concentrations at least in part by detecting optical radiation attenuated by tissue at a measurement site 102. The measurement site 102 can be any location on a patient's body, such as a finger, foot, earlobe, wrist, forehead, or the like.

The pulse oximetry system 800 can include a sensor 801 (or multiple sensors) that is coupled to a processing device or physiological monitor 809. In an embodiment, the sensor 801 and the monitor 809 are integrated together into a single unit. In another embodiment, the sensor 801 and the monitor 809 are separate from each other and communicate with one another in any suitable manner, such as via a wired or wireless connection. The sensor 801 and monitor 809 can be attachable and detachable from each other for the convenience of the user or caregiver, for ease of storage, sterility issues, or the like.

In the depicted embodiment shown in FIG. 8, the sensor 801 includes an emitter 804, a detector 806, and a front-end interface 808. The emitter 804 can serve as the source of optical radiation transmitted towards measurement site 102. The emitter 804 can include one or more sources of optical radiation, such as light emitting diodes (LEDs), laser diodes, incandescent bulbs with appropriate frequency-selective filters, combinations of the same, or the like. In an embodiment, the emitter 804 includes sets of optical sources that are capable of emitting visible and near-infrared optical radiation.

The pulse oximetry system 800 also includes a driver 811 that drives the emitter 804. The driver 111 can be a circuit or the like that is controlled by the monitor 809. For example, the driver 811 can provide pulses of current to the emitter 804. In an embodiment, the driver 811 drives the emitter 804 in a progressive fashion, such as in an alternating manner. The driver 811 can drive the emitter 804 with a series of pulses for some wavelengths that can penetrate tissue relatively well and for other wavelengths that tend to be significantly absorbed in tissue. A wide variety of other driving powers and driving methodologies can be used in various embodiments. The driver 811 can be synchronized with other parts of the sensor 801 to minimize or reduce jitter in the timing of pulses of optical radiation emitted from the emitter 804. In some embodiments, the driver 811 is capable of driving the emitter 804 to emit optical radiation in a pattern that varies by less than about 10 parts-per-million.

The detector 806 captures and measures light from the tissue measurement site 102. For example, the detector 806 can capture and measure light transmitted from the emitter 804 that has been attenuated or reflected from the tissue at the measurement site 102. The detector 806 can output a detector signal 107 responsive to the light captured and measured. The detector 806 can be implemented using one or more photodiodes, phototransistors, or the like. In some embodiments, a detector 806 is implemented in detector package to capture and measure light from the tissue measurement site 102 of the patient. The detector package can include a photodiode chip mounted to leads and enclosed in an encapsulant. In some embodiments, the dimensions of the detector package are approximately 2 square centimeters. In other embodiments, the dimensions of the detector package are approximately 1.5 centimeters in width and approximately 2 centimeters in length.

The front-end interface 808 provides an interface that adapts the output of the detectors 806, which is responsive to desired physiological parameters. For example, the front-end interface 808 can adapt the signal 807 received from the detector 806 into a form that can be processed by the monitor 809, for example, by a signal processor 810 in the monitor 809. The front-end interface 808 can have its components assembled in the sensor 801, in the monitor 809, in a connecting cabling (if used), in combinations of the same, or the like. The location of the front-end interface 808 can be chosen based on various factors including space desired for components, desired noise reductions or limits, desired heat reductions or limits, and the like.

The front-end interface 808 can be coupled to the detector 806 and to the signal processor 810 using a bus, wire, electrical or optical cable, flex circuit, or some other form of signal connection. The front-end interface 808 can also be at least partially integrated with various components, such as the detectors 806. For example, the front-end interface 808 can include one or more integrated circuits that are on the same circuit board as the detector 806. Other configurations can also be used.

As shown in FIG. 8, the monitor 909 can include the signal processor 810 and a user interface, such as a display 812. The monitor 809 can also include optional outputs alone or in combination with the display 812, such as a storage device 814 and a network interface 816. In an embodiment, the signal processor 810 includes processing logic that determines measurements for desired analytes based on the signals received from the detector 806. The signal processor 810 can be implemented using one or more microprocessors or sub-processors (e.g., cores), digital signal processors, application specific integrated circuits (ASICs), field programmable gate arrays (FPGAs), combinations of the same, and the like.

The signal processor 810 can provide various signals that control the operation of the sensor 801. For example, the signal processor 810 can provide an emitter control signal to the driver 811. This control signal can be useful in order to synchronize, minimize, or reduce jitter in the timing of pulses emitted from the emitter 804. Accordingly, this control signal can be useful in order to cause optical radiation pulses emitted from the emitter 804 to follow a precise timing and consistent pattern. For example, when a transimpedance-based front-end interface 808 is used, the control signal from the signal processor 810 can provide synchronization with an analog-to-digital converter (ADC) in order to avoid aliasing, cross-talk, and the like. As also shown, an optional memory 813 can be included in the front-end interface 808 and/or in the signal processor 810. This memory 813 can serve as a buffer or storage location for the front-end interface 808 and/or the signal processor 810, among other uses.

The user interface 812 can provide an output, e.g., on a display, for presentation to a user of the pulse oximetry system 800. The user interface 812 can be implemented as a touch-screen display, a liquid crystal display (LCD), an organic LED display, or the like. In alternative embodiments, the pulse oximetry system 800 can be provided without a user interface 812 and can simply provide an output signal to a separate display or system.

The storage device 814 and a network interface 816 represent other optional output connections that can be included in the monitor 809. The storage device 814 can include any computer-readable medium, such as a memory device, hard disk storage, EEPROM, flash drive, or the like. The various software and/or firmware applications can be stored in the storage device 814, which can be executed by the signal processor 810 or another processor of the monitor 809. The network interface 816 can be a serial bus port (RS-232/RS-485), a Universal Serial Bus (USB) port, an Ethernet port, a wireless interface (e.g., WiFi such as any 802.1x interface, including an internal wireless card), or other suitable communication device(s) that allows the monitor 809 to communicate and share data with other devices. The monitor 809 can also include various other components not shown, such as a microprocessor, graphics processor, or controller to output the user interface 812, to control data communications, to compute data trending, or to perform other operations.

Although not shown in the depicted embodiment, the pulse oximetry system 800 can include various other components or can be configured in different ways. For example, the sensor 801 can have both the emitter 804 and detector 806 on the same side of the tissue measurement site 102 and use reflectance to measure analytes.

Although the foregoing disclosure has been described in terms of certain preferred embodiments, many other variations than those described herein will be apparent to those of ordinary skill in the art.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

While the above detailed description has shown, described, and pointed out novel features as applied to various embodiments, it will be understood that various omissions, substitutions, and changes in the form and details of the systems, devices or algorithms illustrated can be made without departing from the spirit of the disclosure. As will be recognized, certain embodiments of the disclosure described herein can be embodied within a form that does not provide all of the features and benefits set forth herein, as some features can be used or practiced separately from others.

The term "and/or" herein has its broadest, least limiting meaning which is the disclosure includes A alone, B alone, both A and B together, or A or B alternatively, but does not require both A and B or require one of A or one of B. As used herein, the phrase "at least one of" A, B, "and" C should be construed to mean a logical A or B or C, using a non-exclusive logical or.

The apparatuses and methods described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage. Although the foregoing disclosure has been described in terms of certain preferred embodiments, other embodiments will be apparent to those of ordinary skill in the art from the disclosure herein. Additionally, other combinations, omissions, substitutions and modifications will be apparent to the skilled artisan in view of the disclosure herein. Accordingly, the present invention is not intended to be limited by the description of the preferred embodiments, but is to be defined by reference to claims.

Additionally, all publications, patents, and patent applications mentioned in this specification are herein incorporated by reference to the same extent as if each individual publication, patent, or patent application were specifically and individually indicated to be incorporated by reference.

What is claimed is:

1. A physiological monitoring device comprising:
   a plurality of emitters configured to emit light in a first shape;
   a material positioned between the plurality of emitters and a tissue measurement site on a wrist of a user, the material configured to alter the first shape into a second shape by which the light emitted from one or more of the plurality of emitters is distributed onto a surface of the tissue measurement site;
   a plurality of detectors configured to detect the light after attenuation by tissue, the plurality of detectors further configured to output at least one signal responsive to the detected light;
   a surface comprising a dark-colored coating, the surface positioned between the plurality of detectors and the tissue, wherein an opening defined in the dark-colored coating is configured to allow at least a portion of light reflected from the tissue to pass through the surface;
   a light block configured to prevent at least a portion of the light emitted from the plurality of emitters from reaching the plurality of detectors without first reaching the tissue; and
   a processor configured to receive and process one or more signals responsive to the at least one outputted signal and determine a physiological parameter of the user responsive to the one or more signals.

2. The physiological monitoring device of claim 1, further comprising a display configured to present visual feedback responsive to the determined physiological parameter.

3. The physiological monitoring device of claim 2, wherein the display is a touch-screen display.

4. The physiological monitoring device of claim 1, wherein the plurality of emitters and the plurality of detectors are arranged in a reflectance measurement configuration.

5. The physiological monitoring device of claim 1, wherein the light block comprises an at least partially circular shape, and wherein the plurality of emitters are positioned outside the light block and the plurality of detectors are positioned inside the light block.

6. The physiological monitoring device of claim 1, wherein the physiological parameter comprises pulse rate.

7. The physiological monitoring device of claim 1, wherein the material comprises plastic.

8. The physiological monitoring device of claim 1, wherein the material comprises glass.

9. The physiological monitoring device of claim 1, wherein an amount of light transmitted by the material to the tissue measurement site is greater than 90% of the light emitted by the plurality of emitters.

10. The physiological monitoring device of claim 1, wherein the light emitted from the one or more of the plurality of emitters comprises a Gausian intensity profile after interaction with the material.

11. The physiological monitoring device of claim 1, wherein the second shape comprises a circular geometry.

12. The physiological monitoring device of claim 1, wherein the opening defined in the dark-colored coating comprises a width and a length, and wherein the width is larger than the length.

13. The physiological monitoring device of claim 1, wherein the dark-colored coating comprises black.

14. A method of measuring a physiological parameter, the method comprising:
   emitting, from a plurality of emitters, light proximate a wrist of a user in an initial emitted pattern;
   shaping at least a portion of the light emitted from the plurality of emitters before the light reaches a tissue measurement site to define an altered pattern relative to the initial emitted pattern on the tissue measurement site;
   permitting light reflected from tissue of the user to pass through an opening in a dark-colored coating on a surface and detecting, with a detector, at least a portion of the reflected light passing through the opening, wherein the surface is positioned between the detector and the tissue;
   preventing at least a portion of the light emitted from the plurality of emitters from reaching the detector without first reaching the tissue with a light block;
   outputting, from the detector, at least one signal responsive to the detected light; and
   electronically processing one or more signals responsive to the outputted at least one signal to determine a physiological parameter.

15. The method of claim 14, wherein the light block comprises an at least partially circular shape, and wherein the plurality of emitters are positioned outside the light block and the detector is positioned inside the light block.

16. The method of claim 14, further comprising presenting, with a display, visual feedback responsive to the determined physiological parameter.

17. The method of claim 14, wherein the dark-colored coating comprises black.

18. The method of claim 14, wherein the step of shaping the at least the portion of the light emitted from the plurality of emitters is performed with a material comprising at least one of glass and plastic.

19. The method of claim 14, wherein the opening in the dark-colored coating comprises a width and a length, and wherein the width is larger than the length.

20. A physiological monitoring device comprising:
   a plurality of optical sources configured to emit light proximate a wrist of a user;

a material positioned between the plurality of optical sources and a tissue measurement site, wherein the material is configured to alter a shape by which at least a portion of the light emitted from one or more of the plurality of emitters is distributed on the tissue measurement site;

a light block having a circular shape;

a plurality of detectors configured to detect the light after the light passes through a portion of the tissue measurement site bounded by the light block, wherein the plurality of detectors are arranged in an array having a spatial configuration corresponding to a shape of the portion of the tissue measurement site bounded by the circular shaped light block, wherein the plurality of detectors are further configured to output at least one signal responsive to the detected light, and wherein the plurality of optical sources and the plurality of detectors are arranged in a reflectance measurement configuration;

wherein the light block is configured to prevent at least a portion of light emitted from the plurality of optical sources from reaching the plurality of detectors without first reaching the tissue;

a processor configured to receive and process one or more signals responsive to the at least one outputted signal and determine a physiological parameter of the user responsive to the one or more signals; and wherein the physiological monitoring device is configured to transmit physiological parameter data to a separate processor.

21. The physiological monitoring device of claim 20, wherein the material comprises at least one of glass and plastic.

22. The physiological monitoring device of claim 20, wherein the altered shape comprises a width and a length, and wherein the width is different from the length.

23. A system configured to measure one or more physiological parameters of a user, the system comprising:

a physiological monitoring device comprising:

a plurality of emitters configured to emit light proximate a wrist of a user in a first shape;

a material positioned between the plurality of emitters and a tissue measurement site, the material configured to alter the first shape into a second shape by which the light emitted from one or more of the plurality of emitters is distributed on the tissue measurement site;

a plurality of detectors configured to detect the light after attenuation by tissue, the plurality of detectors further configured to output at least one signal responsive to the detected light;

a surface comprising a dark-colored coating, the surface positioned between the plurality of detectors and the tissue, wherein an opening defined in the dark-colored coating is configured to allow at least a portion of light reflected from the tissue to pass through the surface;

a light block configured to prevent at least a portion of light from the plurality of emitters from reaching the plurality of detectors without first reaching the tissue; and a processor configured to receive and process one or more signals responsive to the outputted at least one signal and determine a physiological parameter of the user responsive to the one or more signals; and a processing device configured to wirelessly receive physiological parameter data from the physiological monitoring device, wherein the processing device comprises a user interface, a storage device, and a network interface configured to wirelessly communicate with the physiological monitoring device, and wherein the user interface includes a touch-screen display configured to present visual feedback responsive to the physiological parameter data.

24. The system of claim 23, wherein the system is configured to determine a state of wellness of the user based on the determined physiological parameter.

25. The system of claim 23, wherein the system is configured to determine a trend of wellness of the user based on the determined physiological parameter.

26. The system of claim 23, wherein the visual feedback presented by the touch-screen display is responsive to a pulse rate of the user.

27. The system of claim 23, wherein the material comprises at least one of glass and plastic.

28. The system of claim 23, wherein the second shape comprises a width and a length, and wherein the width is different from the length.

* * * * *

UNITED STATES PATENT AND TRADEMARK OFFICE
CERTIFICATE OF CORRECTION

PATENT NO. : 10,646,146 B2
APPLICATION NO. : 16/532065
DATED : May 12, 2020
INVENTOR(S) : Ammar Al-Ali It is certified that error appears in the above-identified patent and that said Letters Patent is hereby corrected as shown below:

On the Title Page

On Page 4, Column 2, Item (56), Line 36, under U.S. Patent Documents, delete "Bellot" and insert --Bellott--.

On Page 10, Column 2, Item (56), under Other Publications, Line 43, delete "SPo2" and insert --SpO2--.

On Page 10, Column 2, Item (56), Line 49, under Other Publications, delete "Cigilant" and insert --Vigilant--.

On Page 11, Column 1, Item (56), under Other Publications, Line 26, delete "Conferemce" and insert --Conference--.

On Page 11, Column 1, Item (56), under Other Publications, Line 39, delete "Depolyable," and insert --Deployable,--.

On Page 11, Column 2, Item (56), under Other Publications, Line 30, delete "Placementon" and insert --Placement on--.

In the Drawings

On Drawing Sheet 7 of 7, FIG. 8, Reference Number 810, Line 2, delete "PROCESOR" and insert --PROCESSOR--.

In the Specification

Column 1, Line 48, delete "$\mu_{a,\lambda}$" and insert --$\mu_{a,\lambda}$--.

Column 7, Line 52, delete "(also" and insert --also--.

Signed and Sealed this
Eighth Day of September, 2020

Andrei Iancu
*Director of the United States Patent and Trademark Office*

Column 8, Line 1, delete "Gausian" and insert --Gaussian--.

Column 12, Line 37, delete "light emitting" and insert --light-emitting--.

In the Claims

Column 16, Line 16, Claim 10, delete "Gausian" and insert --Gaussian--.